US011747350B2

(12) United States Patent
Kurono et al.

(10) Patent No.: US 11,747,350 B2
(45) Date of Patent: Sep. 5, 2023

(54) BLOOD COAGULATION ANALYZING METHOD, APPARATUS, AND NON-TRANSITORY COMPUTER-READABLE STORAGE MEDIUM FOR DETERMINING OCCURENCE OF AN EARLY REACTION ERROR

(71) Applicant: SYSMEX CORPORATION, Kobe (JP)

(72) Inventors: Hiroshi Kurono, Kobe (JP); Keiichi Yamaguchi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 871 days.

(21) Appl. No.: 16/583,306

(22) Filed: Sep. 26, 2019

(65) Prior Publication Data
US 2020/0103420 A1 Apr. 2, 2020

(30) Foreign Application Priority Data
Sep. 28, 2018 (JP) ................................. 2018-185946

(51) Int. Cl.
*G01N 33/86* (2006.01)
*G01N 21/82* (2006.01)
(Continued)

(52) U.S. Cl.
CPC ............ *G01N 33/86* (2013.01); *G01N 21/82* (2013.01); *G01N 33/4905* (2013.01);
(Continued)

(58) Field of Classification Search
CPC ............... G01N 33/86; G01N 33/4905; G01N 35/00693; G01N 21/82; G01N 21/272
(Continued)

(56) References Cited

U.S. PATENT DOCUMENTS 3,307,392 A * 3/1967 Owen .................. G01N 21/272
422/44
3,458,287 A * 7/1969 William ............... G01N 21/272
435/13
(Continued)

FOREIGN PATENT DOCUMENTS

EP 62616 * 10/1982
EP 3076173 A1 10/2016
(Continued)

OTHER PUBLICATIONS

Extended European search report (EESR) dated Jun. 17, 2020 in a counterpart European patent application.
(Continued)

*Primary Examiner* — Arlen Soderquist
(74) *Attorney, Agent, or Firm* — METROLEX IP LAW GROUP, PLLC

(57) ABSTRACT

A blood coagulation analyzing method according to one or more aspects may include: calculating a coagulation time based on data representing a coagulation curve of a change in an optical detection value of a blood specimen added with a reagent for starting a coagulation reaction; calculating an index value related to derivatives calculated concerning the coagulation curve represented by the data used in the calculating the coagulation time; and determining whether an early reaction error has occurred based on a comparison result obtained by comparing the index value to a predetermined threshold.

19 Claims, 22 Drawing Sheets

(51) Int. Cl.
*G01N 33/49* (2006.01)
*G01N 35/00* (2006.01)

(52) U.S. Cl.
CPC .............. *G01N 35/00693* (2013.01); *G01N 2035/0097* (2013.01); *G01N 2035/00702* (2013.01); *G01N 2333/7454* (2013.01)

(58) Field of Classification Search
USPC .......................................................... 436/69
See application file for complete search history.

(56) References Cited

U.S. PATENT DOCUMENTS

| | | | | |
|---|---|---|---|---|
| 4,109,159 | A * | 8/1978 | Onillon | G01N 21/272 356/442 |
| 4,217,107 | A * | 8/1980 | Saito | G01N 33/4905 73/64.41 |
| 4,454,752 | A * | 6/1984 | Scordato | G01N 33/4905 73/1.02 |
| 4,492,462 | A * | 1/1985 | Pross | G01N 33/4905 356/342 |
| 5,114,860 | A * | 5/1992 | Hayashi | G01N 33/86 436/164 |
| 6,321,164 | B1 * | 11/2001 | Braun | G01N 33/86 702/30 |
| 6,524,861 | B1 * | 2/2003 | Anderson | G01N 33/86 422/65 |
| 6,645,768 | B1 * | 11/2003 | Tejidor | G01N 33/86 436/63 |
| 6,743,596 | B1 * | 6/2004 | Fischer | G01N 33/86 435/13 |
| 7,276,376 | B2 * | 10/2007 | Katayama | G01N 33/4905 436/63 |
| 7,962,292 | B2 * | 6/2011 | Matsuo | G01N 21/82 702/22 |
| 9,581,609 | B2 | 2/2017 | Yabutani et al. | |
| 2003/0138962 | A1 * | 7/2003 | Katayama | G01N 33/4905 435/13 |
| 2003/0228625 | A1 * | 12/2003 | Toh | A61P 7/00 435/7.1 |
| 2004/0053351 | A1 * | 3/2004 | Fischer | G01N 33/86 435/13 |
| 2005/0191751 | A1 * | 9/2005 | Tejidor | G01N 33/86 436/8 |
| 2007/0222973 | A1 * | 9/2007 | Hoshiko | G01N 35/00603 356/436 |
| 2007/0248490 | A1 * | 10/2007 | Matsuo | G01N 33/4905 422/64 |
| 2008/0183431 | A1 * | 7/2008 | Matsuo | G01N 15/12 702/187 |
| 2009/0061468 | A1 * | 3/2009 | Hoshiko | G01N 33/86 435/13 |
| 2011/0014640 | A1 * | 1/2011 | Yamamoto | G01N 35/00603 435/286.1 |
| 2012/0282139 | A1 * | 11/2012 | Makino | G01N 33/4905 422/73 |
| 2013/0344519 | A1 * | 12/2013 | Leong | G01N 33/86 435/13 |
| 2014/0255254 | A1 * | 9/2014 | Yamaguchi | G01N 33/4905 422/73 |
| 2016/0178651 | A1 * | 6/2016 | Shima | G01N 33/4905 435/13 |
| 2016/0291040 | A1 * | 10/2016 | Koshimura | G01N 33/4905 |
| 2016/0291042 | A1 * | 10/2016 | Kumano | G01N 21/82 |
| 2016/0291046 | A1 * | 10/2016 | Yabutani | G01N 35/0092 |
| 2017/0131306 | A1 * | 5/2017 | Tarumi | G01N 21/272 |
| 2018/0120292 | A1 * | 5/2018 | Thomas | G01N 33/48792 |
| 2018/0306820 | A1 * | 10/2018 | Suzuki | G01N 21/82 |

FOREIGN PATENT DOCUMENTS

| | | | | |
|---|---|---|---|---|
| EP | 3315972 | A1 | 5/2018 | |
| JP | 59203959 | A * | 11/1984 | ......... G01N 33/4905 |
| JP | S63-305255 | A | 12/1988 | |
| JP | 4-318463 | | * 11/1992 | |
| JP | H04-318463 | A | 11/1992 | |
| JP | H06-027115 | A | 2/1994 | |
| JP | 2003-169700 | A | 6/2003 | |
| JP | 2007-107889 | | * 4/2007 | |
| JP | 2008209350 | A * | 9/2008 | |
| JP | 2010-217059 | A | 9/2010 | |
| JP | 2016-118442 | A | 6/2016 | |
| JP | 2018-017619 | A | 2/2018 | |
| JP | 2018-072156 | A | 5/2018 | |
| WO | WO-0234110 | A2 * | 5/2002 | ............ G01N 33/86 |
| WO | 2014/162878 | A1 | 10/2014 | |

OTHER PUBLICATIONS

Office Action dated Jun. 30, 2020 in a counterpart Japanese patent application.
Office Action dated Apr. 27, 2021 in a counterpart Japanese patent application.
Japanese Office Action dated Jan. 21, 2020 in a counterpart Japanese patent application.
Invitation pursuant to Rule 63(1) EPC dated Jan. 29, 2020 in a counterpart European patent application.
Communication dated Jun. 20, 2023 in a counterpart European patent application.

* cited by examiner

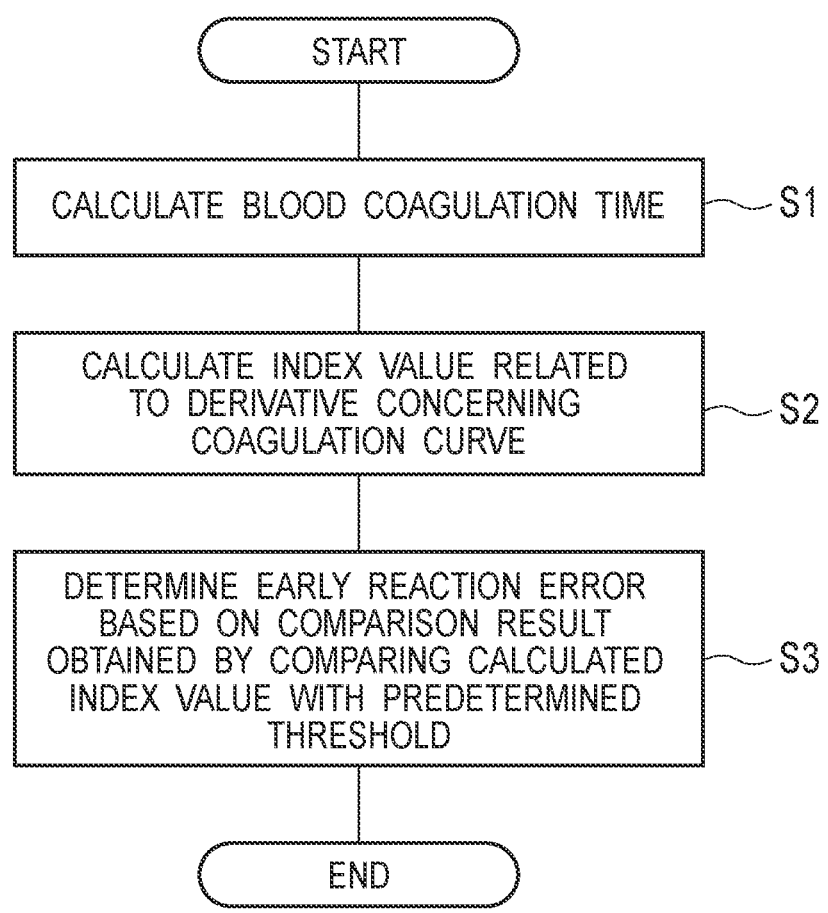

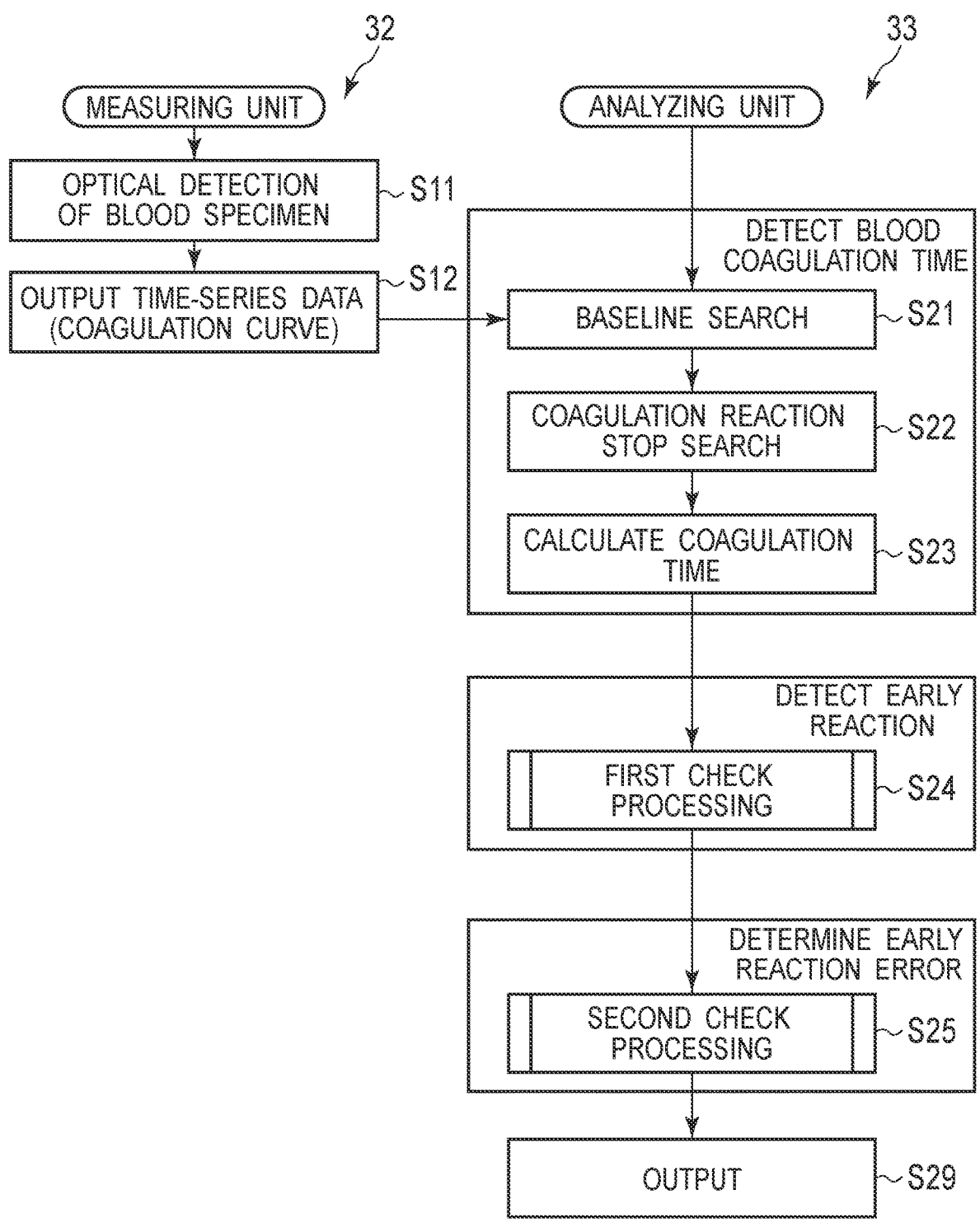

FIG. 13

| Parameter | Slow Reaction | Start Angle | Early% |
|---|---|---|---|
| COAGULATION TIME-min1_time | 10.0 | 1 | 1 |
| |Min1| | 0.1 | - | - |
| Area_1 | - | 1 | - |
| dH_ratio | - | - | 0.2 |

| Parameter | Start Angle | Early% |
|---|---|---|
| RECALCULATED COAGULATION TIME-min1_time | 3.0 | 3.0 |

FIG. 25

|  | Current | New |  |
|---|---|---|---|
| Slow reaction | 1 | No Error | 1 |
|  |  | Coag % Changed | 0 |
| Early% | 5 | Early% | 1 |
|  |  | No Error | 1 |
|  |  | Coag % Changed | 3 |
| Start Angle1 | 1 | No Error | 0 |
|  |  | Coag % Changed | 1 |
| Start Angle2 | 16 | No Error | 11 |
|  |  | Coag % Changed | 5 |
| No error | 4 | No Error | 4 |
| Other error | 1 | No Error | 1 |
| Total | 28 | Early% | 1 |
|  |  | No Error | 18 |
|  |  | Coag % Changed | 9 |

FIG. 26

| NUMBER OF ERE FLAGS BY FIRST CHECK PROCESSING | RESULT OF SECOND CHECK PROCESSING | | RESULT OF THIRD CHECK PROCESSING | |
|---|---|---|---|---|
|  | MAINTAIN ERE FLAG (False positives) | REMOVE ERE FLAG | MAINTAIN ERE FLAG | Coag % Changed |
| 23※ | 10 | 13 | 1 | 9 |

※ IT IS CONFIRMED THAT True error IS ABSENT

FIG. 27

|  | Current | New | |
|---|---|---|---|
| Early% | 11 | Early% | 0 |
|  |  | No Error | 3 |
|  |  | Coag % Changed | 8 |
| Start Angle2 | 58 | No Error | 41 |
|  |  | Coag % Changed | 17 |
| No error | 33 | No Error | 31 |
|  |  | Coag % Changed | 2 |
| Total | 102 | No Error | 75 |
|  |  | Coag % Changed | 27 |

FIG. 28

| NUMBER OF ERE FLAGS BY FIRST CHECK PROCESSING | RESULT OF SECOND CHECK PROCESSING | | RESULT OF THIRD CHECK PROCESSING | |
|---|---|---|---|---|
|  | MAINTAIN ERE FLAG (False positives) | REMOVE ERE FLAG | MAINTAIN ERE FLAG | Coag % Changed |
| 69※ | 25 | 44 | 0 | 25 |

※ IT IS CONFIRMED THAT True error IS ABSENT

BLOOD COAGULATION ANALYZING METHOD, APPARATUS, AND NON-TRANSITORY COMPUTER-READABLE STORAGE MEDIUM FOR DETERMINING OCCURENCE OF AN EARLY REACTION ERROR

CROSS REFERENCE TO RELATED APPLICATIONS

This application claims priority from to prior Japanese Patent Application No. 2018-185946 filed with the Japan Patent Office on Sep. 28, 2018, the entire contents of which are incorporated herein by reference.

BACKGROUND

The disclosure relates a blood coagulation analysis.

Importance of a blood coagulation analysis contributing to control of a blood clot risk, an early diagnosis of thrombosis, and so on has been increasing along with the growth of aging population.

A coagulation time is calculated in the blood coagulation analysis. The coagulation time is calculated from a coagulation curve obtained by optically detecting a turbidity change that occurs in a blood specimen. The coagulation curve sometimes indicates an early reaction. In the early reaction, a blood sample causes a turbidity change different from a normal coagulation reaction for several seconds to several minutes after a reagent is added to the blood sample. Therefore, when the early reaction occurs, the early reaction affects reliability of the coagulation time calculated in the blood coagulation analysis. Note that the early reaction sometimes occurs in, for example, blood collected from a subject to whom a large amount of heparin is administered or a subject of disseminated intracapillary coagulation (DIC).

In recent years, the detection of the early reaction and the calculation of the coagulation time have been automated. When the early reaction is detected, the early reaction is output as data indicating that an early reaction error (hereinafter abbreviated as ERE) may probably have occurred. The ERE is an error in which the early reaction is misrecognized as a coagulation reaction and the coagulation time is erroneously calculated. In the blood coagulation analysis, an occurrence probability of the early reaction is approximately 1%. Concerning data representing a coagulation curve of a blood specimen in which the early reaction is detected, a specialist needs to, for example, check the coagulation curve, individually determine whether the calculated coagulation time is reliable, and perform repreparation of a measurement specimen.

On the other hand, it has been known that, even if the early reaction is detected, the calculated coagulation time is sometimes correct. That is, some data representing the coagulation curve of the blood specimen in which the early reaction is detected does not have significant influence on the calculation of the coagulation time and has no problem in the reliability of the coagulation time automatically calculated. In such a case, even if the early reaction is detected, it is desirable to treat the ERE as not having occurred. There is a demand for a technique for effectively determining a case in which, even if the early reaction is detected, the ERE should be treated as not having occurred.

Japanese Patent Application Publication No. 2018-072156 (Patent Literature 1) discloses a method in which an early reaction is detected by first check processing of detecting a characteristic of an early reaction of a coagulation curve, and it is thereafter determined, in second check processing, whether the coagulation curve is good enough to calculate a coagulation time correctly. In the second check processing, conformity between a shape of the coagulation curve and a shape of a reference coagulation curve is determined.

However, in Patent Literature 1, there is room of improvement concerning accuracy of determining a case in which an ERE does not occur even if an early reaction is detected.

One or more aspects may aim to accurately determine a case in which an ERE does not occur even if an early reaction is detected.

SUMMARY

A blood coagulation analyzing method according to one or more aspects may include: calculating a coagulation time based on data representing a change in an optical detection value of a blood specimen added with a reagent for starting a coagulation reaction; calculating an index value related to derivatives calculated concerning a coagulation curve represented by the data used in the calculating the coagulation time; and determining whether an early reaction error has occurred based on a comparison result obtained by comparing the index value to a predetermined threshold.

A blood coagulation analyzing apparatus according to one or more aspects may include an analysis controller that perform operations including: calculating a coagulation time based on data representing a change in an optical detection value of a blood specimen added with a reagent for starting a coagulation reaction; and determining whether an early reaction error has occurred based on a comparison result obtained by comparing an index value related to derivatives calculated concerning a coagulation curve represented by the data, to a predetermined threshold.

A non-transitory computer-readable storage medium storing a computer program, according to one or more aspects, which when read and executed causes a computer to perform blood coagulation analyzing operations may include: calculating a coagulation time based on data representing a change in an optical detection value of a blood specimen added with a reagent for starting a coagulation reaction; and determining whether an early reaction error has occurred based on a comparison result obtained by comparing an index value related to derivatives calculated concerning a coagulation curve represented by the data, to a predetermined threshold.

A blood coagulation analyzing method according to one or more aspects may include: calculating a coagulation time based on data representing a change in an optical detection value of a blood specimen added with a reagent for starting a coagulation reaction; and outputting the coagulation time based on a comparison result obtained by comparing an index value related to derivatives calculated concerning a coagulation curve represented by the data used in the calculating the coagulation time, to a predetermined threshold.

BRIEF DESCRIPTION OF DRAWINGS

FIG. 2 is a flow diagram illustrating an overview of a flow of processing of a blood coagulation analyzing method according to an embodiment;

FIG. 3 is a flow diagram illustrating an example of a flow of processing of a blood coagulation analyzing method;

FIG. 13 is a diagram illustrating an example of a threshold set for each index value used in second check processing;

FIG. 25 is a diagram illustrating an application example of a blood coagulation analyzing method according to an embodiment;

FIG. 26 is a diagram illustrating effects of second check processing and third check processing of a blood coagulation analyzing method according to an embodiment;

FIG. 27 is a diagram illustrating another application example of a blood coagulation analyzing method according to an embodiment; and FIG. 28 is a diagram illustrating effects of second check processing and third check processing of a blood coagulation analyzing method according to an embodiment.

DETAILED DESCRIPTION

Figure 1A:
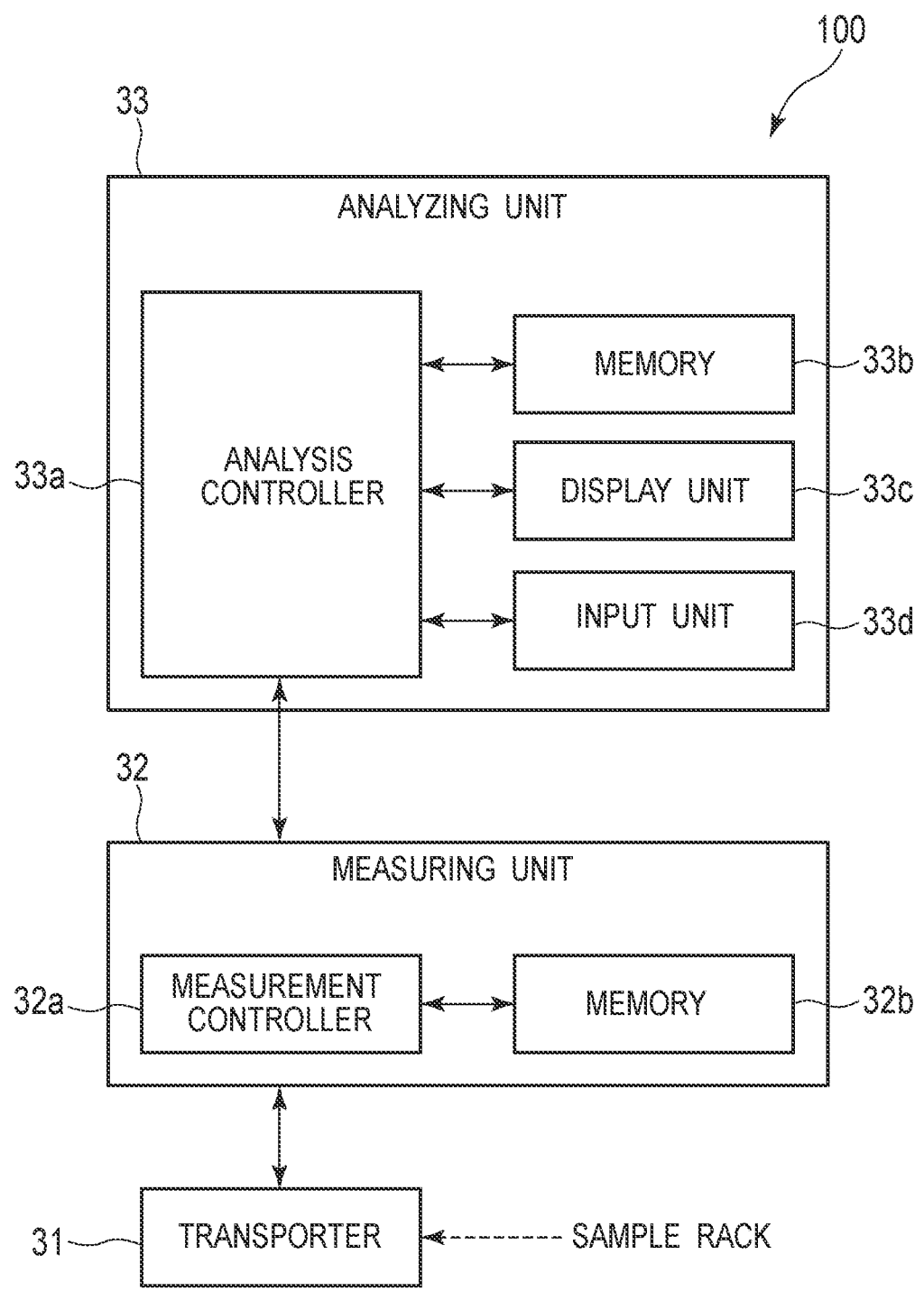
FIG. 1A is a block diagram illustrating a configuration of a blood coagulation analyzing apparatus according to a first embodiment.

In order to solve the problems, a blood coagulation analyzing method according to one or more aspects includes: a coagulation time calculating step (S1) of calculating a coagulation time based on data indicating a change over time of an optical detection value of a blood specimen added with a reagent for starting a coagulation reaction; an index value calculating step (S2) of calculating an index value related to derivatives calculated concerning a coagulation curve represented by the data used to calculate the coagulation time; and a determining step (S3) of determining whether an early reaction error has occurred based on a comparison result obtained by comparing the index value to a predetermined threshold.

When a coagulation curve in which an early reaction is detected is verified by a specialist, the specialist individually determines whether the calculated coagulation time is reliable based on a characteristic of a shape of the coagulation curve represented by the data used to calculate the coagulation time. The index value is a value directly representing the characteristic of the shape of the coagulation curve using the derivatives calculated concerning the coagulation curve represented by the data used to calculate the coagulation time.

With the configuration described above, the index value related to the derivatives calculated concerning the coagulation curve represented by the data used to calculate the coagulation time is calculated. Whether the coagulation time is calculated with an early reaction in the blood sample misrecognized as a coagulation reaction is determined based on the comparison result obtained by comparing the index value to the predetermined threshold. Consequently, even if the early reaction is detected, it is possible to accurately determine whether the coagulation time is calculated with the early reaction misrecognized as the coagulation reaction.

The index value may be selected from the group including of: a time (min1_time) from a first time point (0) when a reagent is added until a second time point when a minimum value of a first derivative calculated concerning the coagulation curve is given; an absolute value (|Min1|) of the minimum value of the first derivative calculated concerning the coagulation curve; an integral value (Area_1) of a difference between the optical detection value in a period from a third time point (bH_time) when a predetermined time elapses from the first time point (0) until a fourth time point (min2_time) when a minimum value of a second derivative calculated based on the coagulation curve is given and the optical detection value at the third time point; and a ratio (dH_ratio) of the difference between the optical detection value at the fourth time point and the optical detection value at the third time point and a difference between the optical direction value at a fifth time point (a coagulation reaction stop point) when the coagulation reaction can be regarded as stopped or substantially ended and the optical detection value at the third time point.

The index value is the value directly indicating the characteristic of the shape of the coagulation curve. By adopting the index value selected from the group including of the values described above, even if the early reaction is detected, it is possible to accurately detect whether the coagulation time is calculated with the early reaction misrecognized as the coagulation reaction.

In the determining step (S3), when a difference between the coagulation time and a time from a first time point when the reagent is added until a second time point when a minimum value of a first derivative calculated concerning the coagulation curve is given is larger than a threshold, it may be determined that the early reaction error has occurred.

It is possible to evaluate the magnitude of influence due to the detected early reaction according to the magnitude of the difference between the coagulation time calculated in the coagulation time calculating step (S1) and the time from the first time point (0) until the second time point.

With the configuration described above, it is possible to appropriately determine reliability of the calculated coagulation time according to the magnitude of influence due to the detected early reaction. Consequently, even if the early reaction is detected, it is possible to accurately determine whether the coagulation time is calculated with the early reaction misrecognized as the coagulation reaction.

The blood coagulation analyzing method may further include a detecting step (S241) of detecting a characteristic indicating the early reaction in the coagulation curve, and, when the characteristic indicating the early reaction is detected, the index value and the predetermined threshold may be compared.

Consequently, when the early reaction is detected, it is possible to appropriately determine whether the early reaction error has occurred.

In the detecting step (S241), the characteristic may include at least one characteristic selected from the group including of: a characteristic that, in the coagulation curve, a time of a change from a first optical detection value (TL1) to a second optical detection value (TL2) is longer than a first reference time (Max Time); a characteristic that, in the coagulation curve, a change in an optical detection value for a predetermined period is larger than a predetermined reference value (Delta); and a characteristic that, in the coagulation curve, a time until a third optical detection value (Check Point) is reached is shorter than a second reference time (Limit).

The influence of the early reaction that should be detected affecting the shape of the coagulation curve can be classified into several typical types. With the configuration described above, it is possible to accurately detect these types in the detecting step (S241).

The determining step (S3) may be performed when at least one characteristic is detected in the detecting step (S241) and may not be performed when a characteristic is not detected.

With the configuration described above, the determining step (S3) is performed when the early reaction is detected in the detecting step (S241). Consequently, the determining step (S3) can be configured to be executed only when necessary.

In the coagulation time calculating step (S1), the coagulation time may be calculated, based on the coagulation curve, as a time in which the blood specimen reaches a coagulation point.

Consequently, it is possible to appropriately calculate the coagulation time based on the coagulation curve.

In the coagulation time calculating step (S1), a sixth time point when the optical detection value is detected may be determined, in which a ratio of a difference from the optical detection value at a third time point (bH_time) when a predetermined time elapses from a time point when the reagent is added, with respect to a difference between the optical detection value at the third time point and the optical detection value at a fifth time point when the coagulation reaction is regarded as stopped or substantially ended is a predetermined ratio (coagulation detection %), and a time from the time point when the reagent is added until the sixth time point may be set as the coagulation time.

Consequently, it is possible to appropriately calculate the coagulation time based on the coagulation curve.

The data representing the coagulation curve may include at least an optical detection value in a period from a coagulation reaction start until a coagulation reaction stop in the blood specimen.

When the early reaction is detected, the coagulation curve does not need to be a coagulation curve represented by data in an entire detection period and only has to include data in a period used to calculate the coagulation time. Therefore, the data representing the coagulation curve only has to include at least an optical detection value in a period from a coagulation reaction start until a coagulation reaction stop in the blood specimen.

The blood coagulation analyzing method may further include a recalculating step (S271) of, when it is determined in the determining step (S3) that the early reaction error has occurred, recalculating the coagulation time with a coagulation reaction start time point in the blood specimen changed from a time point when the coagulation reaction is firstly observed.

Even when the coagulation curve has a shape affected by the early reaction, the coagulation time can be sometimes calculated based on the coagulation curve if a calculation method is changed. With the configuration described above, when it is determined that the early reaction error has occurred, the coagulation time is recalculated with the coagulation reaction start time point in the blood specimen changed. Consequently, it is possible to calculate the coagulation time with high reliability from the coagulation curve having the shape affected by the early reaction.

In the recalculating step, the coagulation reaction start time point may be set to a fourth time point when the optical detection value gives a minimum value of a second derivative calculated concerning the coagulation curve.

The inventors have found that the fourth time point when the minimum value of the secondary differential is given in shapes of a large number of coagulation curves in which the early reaction is detected is a time point when the influence due to the early reaction may be regarded as being substantially eliminated. With the configuration described above, it is possible to calculate the coagulation time with high reliability from the coagulation curve having the shape affected by the early reaction.

The blood coagulation analyzing method may further include a redetermining step (S272) of determining whether the early reaction error has occurred, after the recalculating step (271), based on a difference between the coagulation time calculated in the recalculating step and a time (min1_time) from a first time point when the reagent is added until a second time point when a minimum value of a first derivative calculated concerning the coagulation curve is given.

With the configuration explained above, whether the early reaction error has occurred is determined based on the difference between the coagulation time calculated in the recalculating step (S271) and the time from the first time point when the reagent is added until the second time point when the minimum value of the primary differential of the coagulation curve is given. Consequently, it is possible to appropriately determine whether the coagulation time calculated from the coagulation curve having the shape affected by the early reaction is calculated with the early reaction misrecognized as the coagulation reaction.

An error flag may be displayed on a display when it is determined in the redetermining step (S272) that the coagulation time is calculated with the early reaction in the blood specimen misrecognized as the coagulation reaction.

Consequently, it is possible to clearly inform, for example, a person who performs a blood coagulation analysis that reliability of the calculated coagulation time is low.

An error flag may be displayed on a display when it is determined in the determining step (S3) that the coagulation time is calculated with the early reaction in the blood specimen misrecognized as the coagulation reaction.

Consequently, it is possible to clearly inform, for example, a person who performs a blood coagulation analysis that reliability of the calculated coagulation time is low.

The error flag may be displayed together with the coagulation time.

Consequently, it is possible to clearly inform, for example, a person who performs a blood coagulation analysis that the error flag is an error flag concerning the displayed coagulation time.

The blood coagulation analyzing method may further include an output step (S29) of outputting the coagulation time in an output form depending on a result of the determination in the determining step (S3).

Consequently, it is possible to clearly inform, for example, a person who performs a blood coagulation analysis that the coagulation time is calculated with the early reaction in the blood specimen misrecognized as the coagulation reaction. It is also possible to indicate, for example, a person who performs a blood coagulation analysis whether the calculated coagulation time is a value calculated by a normal method or a value recalculated through the determining step (S3).

A blood coagulation analyzing apparatus (100) according to one or more aspects includes an analysis controller (33a) that executes: processing (S1) of calculating a coagulation time based on data representing a coagulation curve indicating a change over time of an optical detection value of a blood specimen added with a reagent for starting a coagulation reaction; and processing (S3) of determining whether an early reaction error has occurred, based on a comparison result obtained by comparing an index value related to derivatives calculated concerning the coagulation curve, with a predetermined threshold.

With the configuration described above, the blood coagulation analyzing apparatus (100) determines whether the early reaction error has occurred based on the comparison result obtained by comparing the index value related to the derivatives calculated concerning the coagulation curve represented by the data used to calculate the coagulation time, with the predetermined threshold. Consequently, even if the early reaction is detected, the blood coagulation analyzing apparatus (100) can accurately determine whether the coagulation time is calculated with the early reaction misrecognized as the coagulation reaction.

The blood coagulation analyzing apparatus (100) may further include an analysis controller (33a) that further executes processing of outputting the coagulation time in an output form depending on a result of the determination in the determining processing.

Consequently, the blood coagulation analyzing apparatus (100) can clearly inform, for example, a person who performs a blood coagulation analysis that the coagulation time is calculated with the early reaction in the blood specimen misrecognized as the coagulation reaction.

A computer program according to one or more aspects is a computer program for causing a computer (the blood coagulation analyzing apparatus 100) to execute processing of a blood coagulation analysis, the processing of the blood coagulation analysis including: processing (S1) of calculating a coagulation time based on data representing a coagulation curve indicating a change over time of an optical detection value of a blood specimen added with a reagent for starting a coagulation reaction; and processing (S3) of determining whether an early reaction error has occurred based on a comparison result obtained by comparing an index value related to derivatives calculated concerning the coagulation curve, with a predetermined threshold.

With the configuration described above, the computer program causes the computer (the blood coagulation analyzing apparatus 100) to determine whether the coagulation time is calculated with the early reaction in the blood specimen misrecognized as the coagulation reaction, based on the comparison result obtained by comparing the index value related to the derivatives calculated concerning the coagulation curve represented by the data used to calculate the coagulation time, with the predetermined threshold. Consequently, even if the early reaction is detected, the computer (the blood coagulation analyzing apparatus (100)) can accurately determine whether the coagulation time is calculated with the early reaction misrecognized as the coagulation reaction.

The processing of the blood coagulation analysis may further include processing of outputting the coagulation time in an output form depending on a result of the determination in the determining processing.

Consequently, the computer program can clearly inform, for example, a person who performs a blood coagulation analysis that the coagulation time is calculated with the early reaction in the blood specimen misrecognized as the coagulation reaction.

A blood coagulation analyzing method according to one or more aspects includes a coagulation time calculating step (S1) of calculating a coagulation time based on data indicating a change over time of an optical detection value of a blood specimen added with a reagent for starting or initiating a coagulation reaction; and a step (S29) of outputting the coagulation time based on a comparison result obtained by comparing an index value, which is related to derivatives calculated concerning a coagulation curve represented by the data used to calculate the coagulation time, to a predetermined threshold.

With the configuration described above, the calculated coagulation time is output based on the comparison result obtained by comparing the index value, which is related to the derivatives calculated concerning the coagulation curve represented by the data used to calculate the coagulation time, to the predetermined threshold. Consequently, it is possible to output the coagulation time in a form corresponding to whether an early reaction error has occurred. Accordingly, it is possible to clearly inform a level of reliability of the output coagulation time to, for example, a person who performs a blood coagulation analysis.

The blood coagulation analyzing method may further include a detecting step (S241) of detecting a characteristic indicating the early reaction in the coagulation curve, and, when the characteristic indicating the early reaction is detected, the index value and the predetermined threshold may be compared.

Consequently, when the early reaction is detected, it is possible to appropriately determine whether the early reaction error has occurred.

In the detecting step (S241), the characteristic may include at least one characteristic selected from the group including of: a characteristic that, in the coagulation curve, a time of a change from a first optical detection value (TL1) to a second optical detection value (TL2) is longer than a first reference time (Max Time); a characteristic that, in the coagulation curve, a change in an optical detection value for a predetermined period is larger than a reference value (Delta); and a characteristic that, in the coagulation curve, a time until a third optical detection value (Check Point) is reached is shorter than a second reference time (Limit).

With the configuration described above, in the detecting step (S241), it is possible to accurately detect a type of the early reaction.

According to one or more aspects, it is possible to accurately determine a case in which an ERE does not occur even if an early reaction is detected.

First Embodiment

A first embodiment is explained in detail below.

(A Blood Coagulation Analyzing Apparatus 100)

First, the configuration of a blood coagulation analyzing apparatus 100 is explained with reference to FIGS. 1A to 2. FIG. 1A is a block diagram of the blood coagulation analyzing apparatus 100 according to a first embodiment. FIG. 2 is a flowchart illustrating an overview of a flow of processing of a blood coagulation analyzing method according to an embodiment. The blood coagulation analyzing apparatus 100 illustrated in FIG. 1A executes the blood coagulation analyzing method illustrated in FIG. 2.

As illustrated in FIG. 1A, the blood coagulation analyzing apparatus 100 includes a transporter 31, a measuring unit 32, and an analyzing unit 33.

Figure 7:
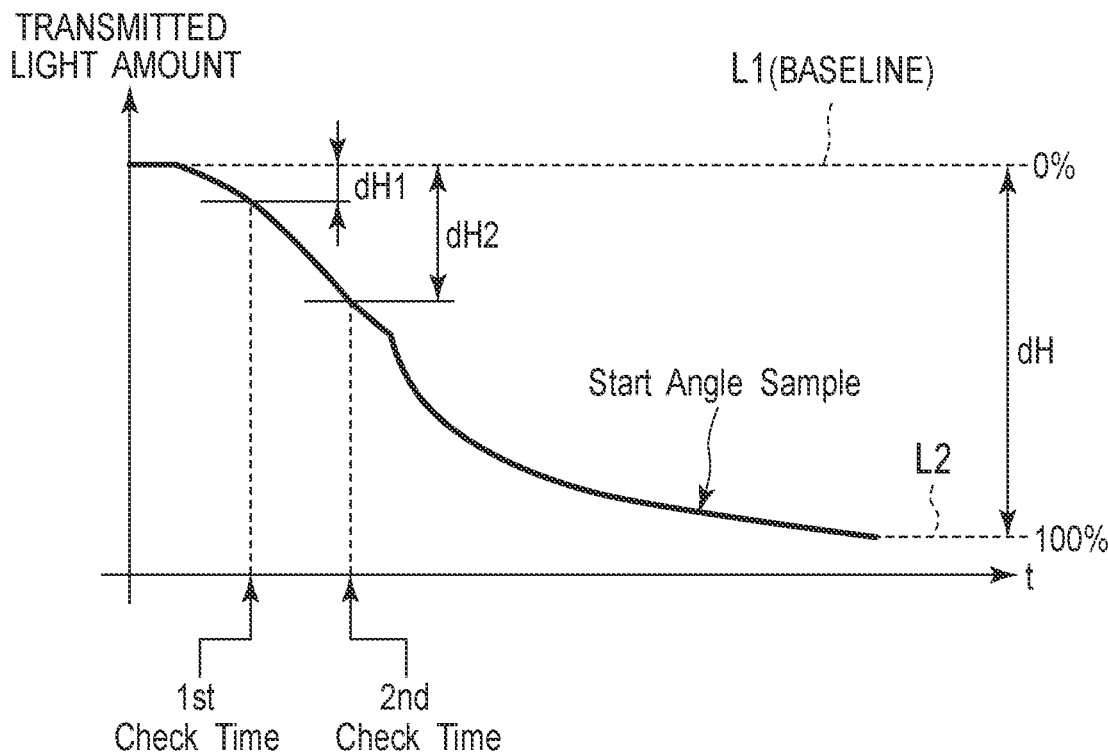
FIG. 7 is a diagram illustrating an overview of a Start Angle check.
Figure 8:
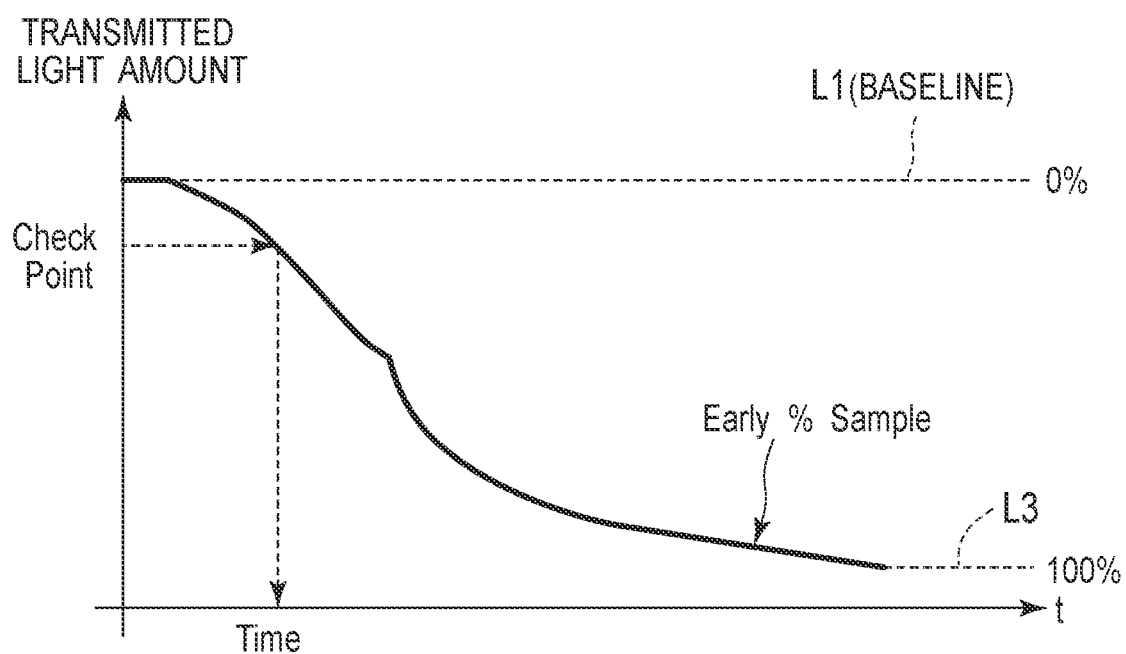
FIG. 8 is a diagram illustrating an overview of an Early % check.

The measuring unit 32 includes a measurement controller 32a, a memory 32b, and various mechanism units illustrated in FIGS. 7 and 8. The measurement controller 32a is, for example, a CPU. The memory 32b is, for example, a ROM, a RAM, or a hard disk. The measurement controller 32a controls units in the measuring unit 32 and the transporter 31 according to programs and data stored in the memory 32b. The measurement controller 32a aspirates a sample supplied by the transporter 31, performs measurement concerning a blood coagulation test for the sample, and transmits a result of the measurement to the analyzing unit 33.

The analyzing unit 33 includes an analysis controller 33a, a memory 33b, a display unit 33c, and an input unit 33d. The analysis controller 33a is, for example, a CPU. The memory 33b is, for example, a ROM, a RAM, or a hard disk. The analysis controller 33a controls units in the analyzing unit 33 and the measuring unit 32 according to programs and data stored in the memory 33b. The display unit 33c is, for example, a liquid crystal display. The input unit 33d is, for example, a mouse and a keyboard. The display unit 33c and the input unit 33d may be integrally configured by a touch panel-type display or the like.

The analysis controller 33a performs an analysis concerning a blood coagulation test on a sample based on a measurement result received from the measuring unit 32. Specifically, the analysis controller 33a performs analyses concerning measurement items such as PT, APTT, Fbg, an exogenous coagulation factor, an endogenous coagulation factor, a coagulation XIII-th factor, HpT, TTO, FDP, D dimer, PIC, FM, ATIII, Plg, APL, PC, VWF:Ag, VWF:RCo, ADP, collagen, and epinephrine.

(The Measuring Unit 32 and the Transporter 31)

Figure 1B:
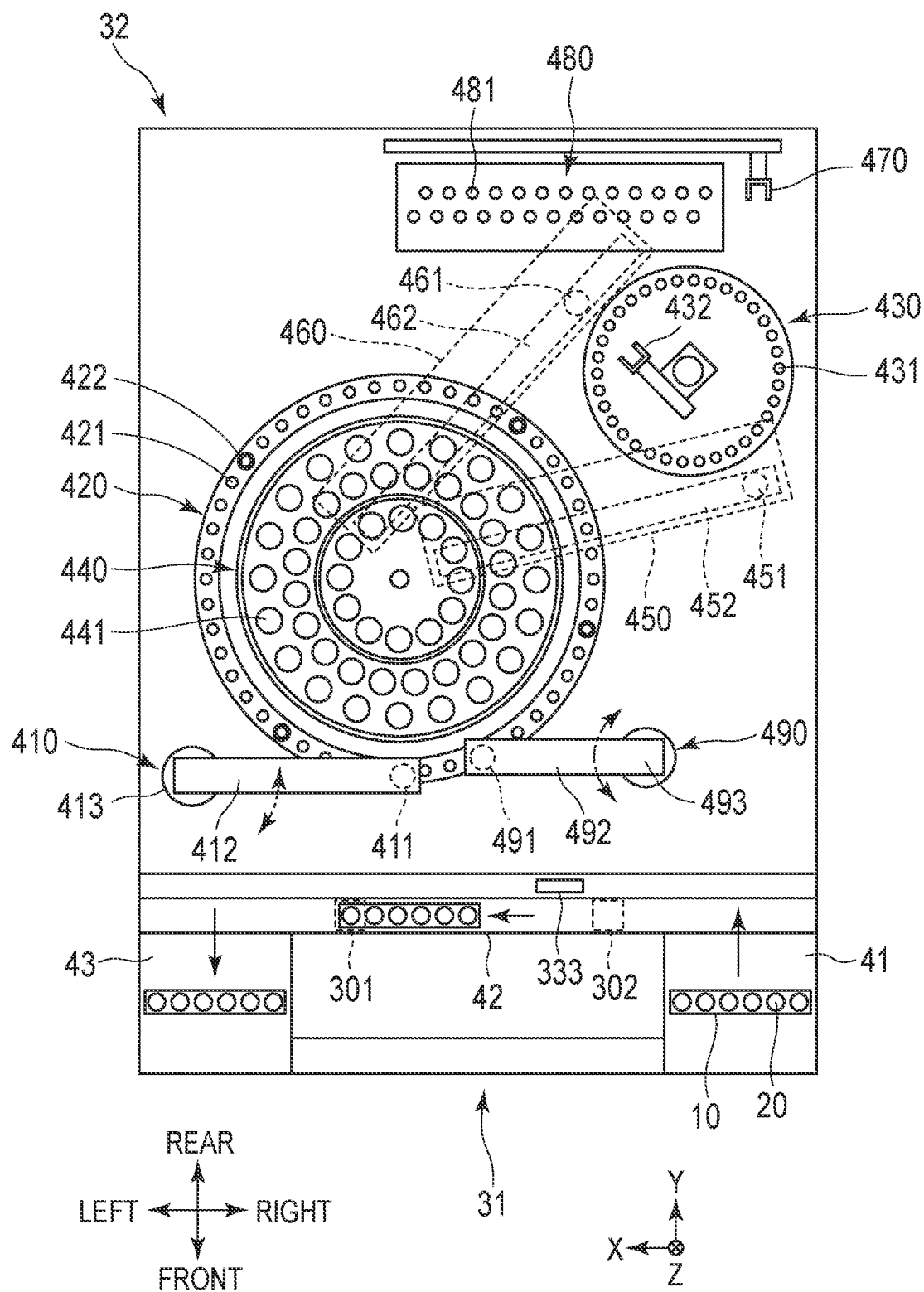
FIG. 1B is a plan diagram schematically illustrating a configuration of a transporter and a measuring unit of a blood coagulation analyzing apparatus according to a first embodiment viewed from above.

As illustrated in FIG. 1B, the measuring unit 32 is arranged behind the transporter 31. The measuring unit 32 performs measurement concerning a blood coagulation test. Therefore, in a first embodiment, a sample stored in a sample container 20 is plasma.

The transporter 31 conveys a sample rack 10 to thereby convey the sample container 20 held by the sample rack 10 to an aspirating position 301 where the measuring unit 32 aspirates the sample.

Note that liquid stored in the sample container 20 as the sample is not limited to the plasma. That is, the sample stored in the sample container 20 is not limited to the plasma and may be whole blood, serum, urine, lymph, celomic fluid, or the like. For example, when the measuring unit 32 performs measurement concerning a blood cell test on the sample, the sample can be whole blood. For example, when the measuring unit 32 performs measurement concerning a blood coagulation test, an immune test, or a biochemical test on the sample, the sample can be plasma. For example, when the measuring unit 32 performs measurement concerning the immune test or the biochemical test on the sample, the sample can be serum.

The measuring unit 32 includes a sample dispensing unit 410, a reaction container table 420, a heating table 430, a reagent table 440, reagent dispensing units 450 and 460, a transferring unit 470, a detecting unit 480, and a sample dispensing unit 490.

The sample dispensing unit 410 lowers an aspirator 411 from an upper side and pierces a plug body 210 through the sample container 20 positioned in the aspirating position 301. The sample dispensing unit 410 aspirates the sample from the sample container 20 via the aspirator 411 and discharges the aspirated sample to a reaction container 422 held by holding holes 421 of the reaction container table 420.

Like the sample dispensing unit 410, the sample dispensing unit 490 includes an aspirator 491, an arm 492, and a mechanism unit 493. The aspirator 491 is set at the distal end of the arm 492. The aspirator 491 is configured by a nozzle. The sample dispensing unit 490 is used for aspirating a very small amount of the sample from the sample container 20, in which an opening 221 is opened, the distal end of the aspirator 411 is formed in a flat shape. The mechanism unit 493 is configured to rotate the arm 492 in the circumferential direction and move the arm 492 in the up-down direction. Consequently, the aspirator 491 is movable in the circumferential direction and the up-down direction.

The sample dispensing unit 490 lowers the aspirator 491 from the upper side and inserts the aspirator 491 into the sample container 20 positioned in an aspirating position 302 on a conveying path 42a of a rack transporter 42. The sample dispensing unit 490 aspirates the sample from the sample container 20 via the aspirator 491 and discharges the aspirated sample to the reaction container 422 held in the holding holes 421 of the reaction container table 420.

The reaction container table 420 has a ring shape in a plan view and is arranged on the outer side of the reagent table 440. The reaction container table 420 is configured to be rotatable in the circumferential direction. The reaction container table 420 includes holding holes 421 for holding the reaction container 422.

The heating table 430 includes holding holes 431 for holding the reaction container 422 and a transferring unit 432 for transferring the reaction container 422. The heating table 430 has a circular contour in a plan view and is configured to be rotatable in the circumferential direction. The heating table 430 heats the reaction container 422 set in the holding holes 431 to 37° C.

When the sample is discharged to the reaction container 422 held by the reaction container table 420, the reaction container table 420 is rotated and the reaction container 422 storing the sample is transferred to the vicinity of the heating table 430. The transferring unit 432 of the heating table 430 grips the reaction container 422 and sets the reaction container 422 in the holding holes 431 of the heating table 430.

The reagent table 440 is configured to be capable of setting reagent containers 441 storing a reagent used for measurement concerning a blood coagulation test. The reagent table 440 is configured to be rotatable in the circumferential direction. The reagent containers 441 storing the reagent used for measurement of measurement items are set on the reagent table 440.

The reagent dispensing unit 450 includes a nozzle 451 and a mechanism unit 452. The mechanism unit 452 is configured to move the nozzle 451 in the horizontal direction to traverse the reagent table 440 and move the nozzle 451 in the up-down direction. Similarly, the reagent dispensing unit 460 includes a nozzle 461 and a mechanism unit 462. The mechanism unit 462 moves the nozzle 461 in the horizontal direction to traverse the reagent table 440 and move the nozzle 461 in the up-down direction. The reagent dispensing units 450 and 460 are set on the lower side of a housing upper surface of the measuring unit 32.

The reagent dispensing units 450 and 460 dispense the reagent into the reaction container 422 heated by the heating table 430. In the dispensing of the reagent, the transferring unit 432 or the transferring unit 470 takes out the reaction container 422 from the holding holes 431 of the heating table 430 and positions the reaction container 422 in a predetermined position near the heating table 430. The reagent dispensing units 450 and 460 aspirate the reagent from the reagent containers 441 via the nozzles 451 and 461 and discharge the aspirated reagent to the reaction container 422. Consequently, the reagent is mixed in the sample and a measurement specimen is prepared. Thereafter, the transferring unit 470 sets the reaction container 422 in holding holes 481 of the detecting unit 480.

A measurement principle of the detecting unit 480 is, for example, a coagulation method, a synthetic substrate method, immunonephelometry, or an agglutination method. The detecting unit 480 includes holding holes 481. The detecting unit 480 irradiates light on the reaction container 422 set in the holding holes 481, receives the light transmitted through a measurement specimen, and outputs a signal corresponding to reception intensity. The measurement controller 32a of the measuring unit 32 stores, as a measurement result, a signal output from the detecting unit 480 and transmits the measurement result to the analyzing unit 33.

(Overview of Processing of the Blood Coagulation Analyzing Apparatus 100)

The measuring unit 32 outputs data representing a coagulation curve indicating a change over time of an optical detection value of a blood specimen added with a reagent. The analyzing unit 33 calculates a coagulation time using the coagulation curve acquired from the measuring unit 32 (step S1 in FIG. 2). Subsequently, the analyzing unit 33 calculates an index value indicating a parameter concerning derivatives of the coagulation curve represented by the data used to calculate the coagulation time (step S2 in FIG. 2). In other words, the analyzing unit 33 calculates an index value related to derivatives calculated concerning the coagulation curve represented by the data used to calculate the coagulation time. The calculated index value is a value indicating a characteristic of a shape of the coagulation curve. Further, the analyzing unit 33 determines an early reaction error (hereinafter described as ERE) based on a comparison result obtained by comparing the index value calculated in step S2 with a predetermined threshold (step S3 in FIG. 2).

The ERE means that a coagulation time is erroneously calculated with an early reaction misrecognized as a coagulation reaction and. "Determine an ERE" in step S3 means to determine whether the coagulation time is calculated in step S1 with an early reaction in a blood specimen misrecognized as a coagulation reaction.

In measurement of a coagulation time in a blood coagulation analysis, an early reaction progresses in a blood specimen added with a reagent. Various early reactions can be measured for blood specimens according to chyle of a blood sample, an agitation state after addition of a specimen for measurement to the blood sample, an amount of the blood specimen, and the like. The measured early reaction is measured as a change over time of an optical detection value in the blood specimen. Therefore, a change over time related to original blood coagulation and a change over time related to the early reaction are mixed in the data representing the coagulation curve output from the measuring unit 32. When the influence due to the change over time related to the early reaction is large in the coagulation curve, it is likely that the analyzing unit 33 erroneously calculates a coagulation time in step S1 (that is, an ERE occurs).

The inventors have focused on the fact that, even when it is determined by the determining method in the past that an ERE has occurred, a coagulation time sometimes can be correctly calculated from an obtained coagulation curve. The inventors have found that a coagulation time sometimes can be correctly calculated even when influence due to an early reaction is large if a step for determining an ERE based on a comparison result obtained by comparing an index based on a shape of the coagulation curve with a predetermined threshold is introduced.

Therefore, after calculating the coagulation time in step S1, in step S2, the analyzing unit 33 of the blood coagulation analyzing apparatus 100 determines an ERE based on a comparison result obtained by comparing an index based on a shape of the coagulation curve with a predetermined threshold. It is possible to accurately determine the ERE by comparing the index based on the shape of the coagulation curve with the predetermined threshold.

Processing respectively performed by the measuring unit 32 and the analyzing unit 33 is explained below with reference to FIG. 3. FIG. 3 is a flowchart illustrating an example of a flow of processing of a blood coagulation analyzing method.

<The Measuring Unit 32>

The measuring unit 32 is a device that outputs, to the analyzing unit 33, a detection value (for example, an optical detection value) detected in a specimen prepared using a sample such as blood collected from a subject. More specifically, the measuring unit 32 may be a device that performs, for example, measurement for a blood coagulation analysis according to a coagulation method. In the coagulation method, after a quantified blood sample is heated for a fixed time, a reagent is added to the blood sample to prepare a blood specimen, light is irradiated on the blood specimen, and a process of coagulation of blood is detected as a change in an optical characteristic of the blood specimen.

The measuring unit 32 may automatically perform the preparation of the blood specimen and the detection of the optical characteristic of the blood specimen. The measuring unit 32 heats the blood sample, adds the reagent to the heated blood sample, and prepares the blood specimen. The reagent is, for example, a reagent for activated partial thromboplastin time (APTT) measurement. The blood specimen is conveyed to the measuring unit 32. In step S11 in FIG. 3, the measuring unit 32 performs optical detection of the blood specimen.

For optical detection, the measuring unit 32 irradiates light on the blood specimen. As the irradiated light, for example, light from a halogen lamp or an LED can be used. The measuring unit 32 outputs, as an optical detection value, an electric signal corresponding to an amount of light received from the blood specimen. The measuring unit 32 may receive transmitted light from the blood specimen or may detect scattered light. Note that, when the measuring unit 32 detects the transmitted light, a detected light amount decreases as a coagulation reaction progresses. On the other hand, when the measuring unit 32 detects the scattered light, a detected light amount increases as the coagulation reaction progresses. In the following explanation, it is assumed that the measuring unit 32 detects the transmitted light.

When the coagulation reaction of the blood specimen progresses, since turbidity of the blood specimen increases, an amount of light transmitted through the blood specimen changes. The measuring unit 32 detects a process of coagulation of blood as a change over time of a transmitted light amount.

The measuring unit 32 converts the optical detection value into digital data and transmits the digital data to the analyzing unit 33. The digital data transmitted to the analyzing unit 33 is time-series data of the optical detection value in a detection period from a start until an end of detection in the measuring unit 32. As explained above, the time-series data is data obtained by detecting the process of coagulation of blood as a change over time of a transmitted light amount and is data representing a coagulation curve. For example, a sampling time interval of the data representing the coagulation curve is 0.1 second. A time from the start to the completion of detection is, for example, a maximum of one hour.

In steps S21 to S23 in FIG. 3, the analysis controller 33a of the analyzing unit 33 executes processing of calculating a coagulation time based on the data representing the coagulation curve received from the measuring unit 32. In an embodiment, the calculated coagulation time is activated partial thromboplastin time (APTT). In measurement of the APTT, an early reaction easily occurs. A method of calculating a coagulation time is explained below.

Subsequently, in step S24, the analysis controller 33a performs first check processing of detecting an early reaction (step S24). The first check processing is processing of detecting a characteristic indicating the early reaction. The analysis controller 33a performs second check processing on data representing the coagulation curve of the blood specimen from which the characteristic indicating the early reaction is detected in the first check processing (step S25). The second check processing is processing of calculating an index value related to derivatives calculated concerning the coagulation curve (corresponding to step S2 in FIG. 2) and determining an ERE based on a comparison result obtained by comparing the index value with a predetermined threshold (corresponding to step S3 in FIG. 2). Note that "determining an ERE" means to determine whether an ERE has occurred and, more specifically, means to determine whether, in the calculation of the coagulation time, the coagulation time is calculated with the early reaction misrecognized as the coagulation reaction.

That is, the data representing the coagulation curve of the blood specimen, from which the characteristic indicating the early reaction is detected, is further subjected to the second check processing in step S25. In the second check processing, the analysis controller 33a classifies data representing coagulation curves of blood specimens based on characteristics indicating early reactions detected in the coagulation curves of the blood specimens. Note that examples of the characteristics indicating the early reactions used in the classification in the second check processing include "Slow Reaction", "Start Angle", and "Early %".

Specifically, in the first check processing, the analysis controller 33a sets an ERE tag in the data representing the coagulation curves of the blood specimens in which the early reaction is detected among the data representing the coagulation curves of the blood specimens. Subsequently, the analysis controller 33a performs the second check processing on the data representing the coagulation curves of the blood specimens in which the ERE tag is set. Note that "set the ERE tag" means to give the ERE tag.

In the second check processing, the analysis controller 33a classifies the data representing the coagulation curves of the blood specimens into any one of "Slow Reaction", "Start Angle", and "Early %". The analysis controller 33a determines whether the set ERE tag is removed or maintained in the classified data representing the coagulation curves of the blood specimens.

When the ERE tag is removed, the analysis controller 33a causes the display unit 33c to display the coagulation time calculated in step S23. On the other hand, when the ERE tag is maintained, the analysis controller 33a adds an error indication indicating that reliability is low and causes the display unit 33c to display the coagulation time calculated in step S23.

The first check processing is processing of detecting presence of an early reaction that can be an obstacle of calculation of a coagulation time. The second check processing is processing of determining whether the coagulation curve is enough so that the reliability of the coagulation time calculated in step S1 can be considered high, even if an early reaction is detected.

In step S29, the analysis controller 33a outputs the coagulation time in an output form depending on a determination result in step S25. When it is determined in step S25 that the coagulation time is calculated with the early reaction in the blood specimen misrecognized as the coagulation reaction, the analysis controller 33a may cause the display unit 33c to display an error flag (for example, error indication). The analysis controller 33a may cause the display unit 33c to display the error flag together with the coagulation time. Note that the output in step S29 may be transmission of a processing result to another computer.

(Calculation of a Coagulation Time)

Figure 4:
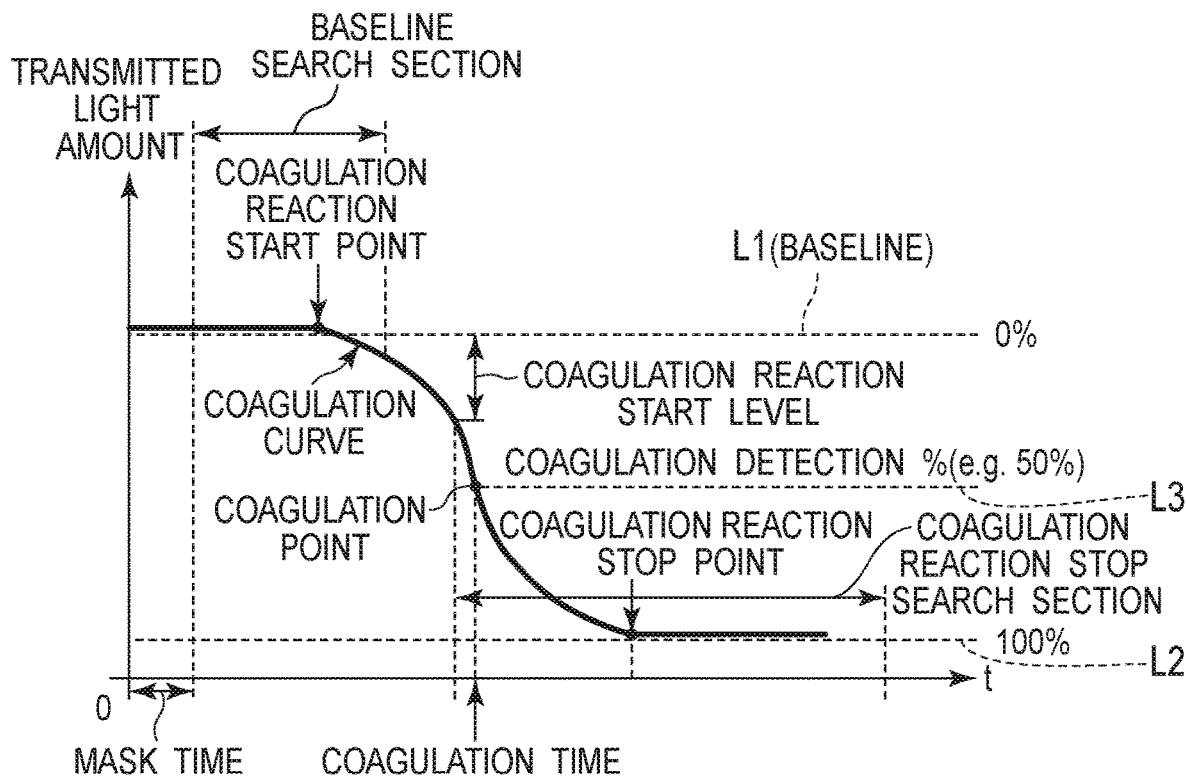
FIG. 4 is a diagram illustrating a basic shape of a coagulation curve used to calculate a coagulation time.

Processing in which the analysis controller 33a calculates a coagulation time based on the data representing the coagulation curve received from the measuring unit 32 is explained with reference to FIG. 4. FIG. 4 is a diagram illustrating a basic shape of a coagulation curve used to calculate a coagulation time. Note that a percent detection method is explained as an example. However, not only this, but, other publicly-known detection methods can be applied.

FIG. 4 illustrates a basic shape of a coagulation curve used to calculate a coagulation time. As illustrated in FIG. 4, a shape of a general coagulation curve is, for example, a shape conforming to a sigmoid curve. The sigmoid curve has a shape similar to sigma of a word end form of a Greek character or "s" of a Latin character. The sigmoid curve only has to have a shape similar to sigma of the word end form or "s" and includes, for example, a so-called logistic curve or Gompertz curve. The sigmoid curve includes, besides a curve having a first shape, a value of the vertical axis of which increases as a value of the horizontal axis of which increases, a curve having a second shape, a value of the vertical axis of which decreases as a value of the horizontal axis of which increases. The shape illustrated in FIG. 3 is the second shape. Note that, when the optical detection value is a transmitted light amount, the general coagulation curve has the second shape illustrated in FIG. 4. However, when the optical detection value is a scattered light amount, the general coagulation curve has the first shape.

As illustrated in FIG. 4, in the case of a general coagulation curve without an abnormality (that is, in which an early reaction is not detected), a transmitted light amount before a coagulation reaction start is substantially fixed. The transmitted light amount monotonously decreases according to a start of a coagulation reaction. A transmitted light amount after a stop or an end of the coagulation reaction is substantially fixed. However, when an abnormal reaction such as an early reaction occurs, deviation of the shape of the coagulation curve from the basic shape illustrated in FIG. 4 sometimes increases.

A coagulation time is calculated based on the premise that the coagulation curve takes the shape illustrated in FIG. 4. FIG. 4 illustrates a percent detection method as an example of a method of calculating a coagulation time. The percent detection method is a method of setting a transmitted light amount serving as a baseline L1 before confirmation of progress of a coagulation reaction to 0%, setting a transmitted light amount (L2) at a coagulation reaction stop point to 100%, and calculating, as a coagulation time, a time when the transmitted light amount reaches the coagulation detection %. The coagulation detection % is set as a value of a predetermined ratio to an interval between the transmitted light amount in the baseline L1 and the transmitted light amount at the coagulation reaction stop point. The coagulation detection % is used to search for a coagulation point where the transmitted light amount changes from the baseline L1 by a predetermined ration (the coagulation detection %). The coagulation detection % is set to a value larger than 0 and smaller than 100. The coagulation detection % is set to, for example, 50%.

In step S21 in FIG. 3, the analysis controller 33a searches for a point where the transmitted light amount is the largest (a coagulation reaction start point) in a baseline search section in FIG. 4 in the data representing the coagulation curve. The baseline search section is a predetermined period from a detection start (for example, a period until 60 seconds after the detection start) and is a period excluding a predetermined mask time set immediately after the detection start (a 0 second time point). Among the data representing the coagulation curve, data corresponding to the baseline search section is used for the baseline search. Note that the mask time is, for example, approximately several seconds. The analysis controller 33a determines, as the baseline L1, the transmitted light amount at the searched coagulation reaction start point. Note that the baseline L1 is referred to as base optical detection value as well Subsequently, in step S22 in FIG. 3, the analysis controller 33a searches for a coagulation reaction stop in the data representing the coagulation curve. The coagulation reaction stop is searched in a coagulation reaction stop search section, which is a period after a time point when a difference between the baseline L1 and the transmitted light amount exceeds a predetermined coagulation reaction start level (see FIG. 4). Among the coagulation curve data, data corresponding to the coagulation reaction stop section is used for the search for the coagulation reaction stop. In the search for the coagulation reaction stop, a coagulation reaction stop point where a change of transmitted light due to the coagulation reaction stop decreases is searched. A line L2 indicates the transmitted light amount at the coagulation reaction stop time, and an optical detection value on this line is referred to as stop time optical detection value.

Subsequently, in step S23 in FIG. 3, the analysis controller 33a calculates a coagulation time based on the percent detection method. Specifically, the analysis controller 33a sets a transmitted light amount in the baseline L1 to 0%, sets a transmitted light amount at the coagulation reaction stop point (the stop time optical detection value) at the coagulation reaction stop point to 100%, and determines, as the coagulation time, a time when the transmitted light amount reaches the coagulation detection % (for example, 50%).

That is, the analysis controller 33a determines a sixth time point when the optical detection value is detected, in which a ratio of a difference from the optical detection value at a third time point when a predetermined time elapses from a time point when the reagent is added, with respect to a difference between the optical detection value at the third time point and the optical detection value at a fifth time point when the coagulation reaction is regarded as stopped is a predetermined ratio (for example, 50%). The analysis controller 33a sets a time from the time point when the reagent is added until the sixth time point as the coagulation time. The third time point may be a time point indicating an intersection of the baseline L1 and the coagulation curve. The fifth time point may be a time point indicating an intersection of the line L2 and the coagulation curve. Note that a point on the coagulation curve at the sixth time point can be described as "coagulation point".

First Check Processing

Figure 5:
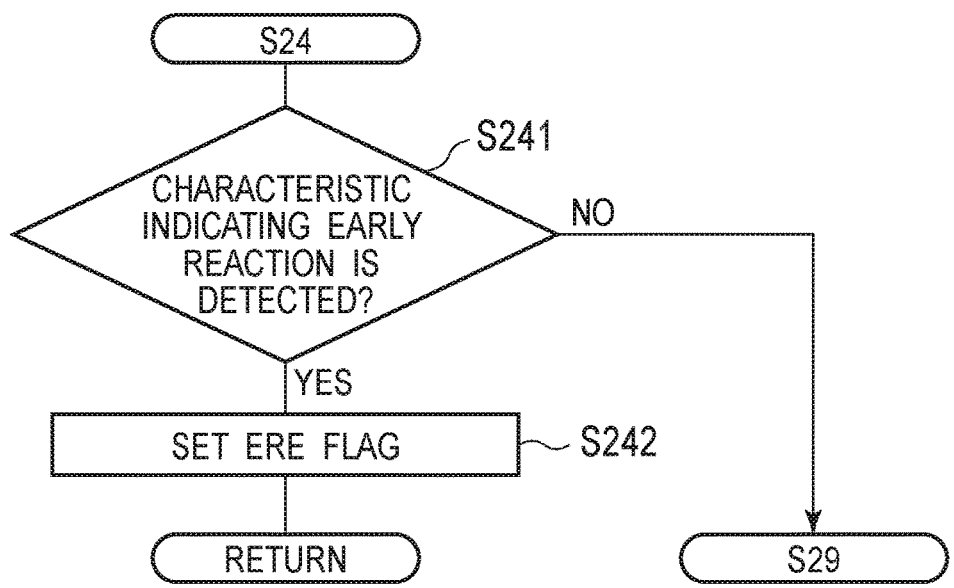
FIG. 5 is a flow diagram illustrating an example of a flow of first check processing.

The first check processing (step S24 in FIG. 3) is explained with reference to FIG. 5 and FIGS. 6 to 8. FIG. 5 is a flowchart illustrating an example of a flow of the first check processing. The first check processing is processing of detecting a characteristic indicating an early reaction.

In order to guarantee reliability of the coagulation time calculated in step S23 in FIG. 3, the analysis controller 33a performs processing of determining presence or absence of an abnormality that occurs in a measurement specimen. The abnormality includes an ERE. Note that the determination of abnormality presence or absence may include determination of presence or absence of an abnormality other than the ERE.

As explained above, in an embodiment, the processing concerning an ERE includes the first check processing in step S24 in FIG. 3. In the first check processing, a characteristic indicating the early reaction in the coagulation curve is detected. In step S241 in FIG. 5, the analysis controller 33a checks presence or absence of the following three characteristics as the characteristic indicating the early reaction. Note that the characteristic indicating the early reaction may be a part of the following three characteristics or may include other characteristics.

Slow Reaction: In a coagulation curve illustrated in FIG. 6, a time (Time2−Time1) of a change from a first optical detection value TL (a first value) to a second optical detection value TL2 (a second value) is longer than a first reference period (Max time). The first reference period is a maximum value of a time (Time2−Time1) of a change from the first optical detection value TL1 to the second optical detection value TL2 in a coagulation curve in which an early reaction is not detected.

Start Angle: In a coagulation curve illustrated in FIG. 7, a change (dH2−dH1) of an optical detection value for a predetermined period (1st check time to 2nd check time) is larger than the predetermined reference value (Delta). The predetermined reference value (Delta) is a maximum value of the change (dH2−dH1) of the optical detection value at 1st check time to 2nd check time in the coagulation curve in which an early reaction is not detected.

Early %: In a coagulation curve illustrated in FIG. 8, a time until a third optical detection value ("Check Point" in the figure) is reached is shorter than a second reference time (Limit). The second reference time (Limit) is a minimum value of a time until the third optical detection value Check Point is reached in a coagulation curve in which an early reaction is not detected.

When at least one characteristic among Slow Reaction, Start Angle, and Early % described above is detected in the coagulation curve, in step S242, the analysis controller 33a provisionally sets an ERE flag. Note that, in step S242, the analysis controller 33a may set a Slow Reaction flag, a Start Angle flag, and an Early % flag. When a characteristic indicating an early reaction is not detected at all, the analysis controller 33a proceeds to step S29 without setting a flag indicating an ERE. That is, an ERE is treated as not having occurred in the coagulation time calculated in step S23 in FIG. 3. Note that, when the ERE flag is set, the analysis controller 33a subsequently performs the second check processing in step S25 in order to confirm whether the set ERE flag may be maintained. The second check processing is explained below.

(Characteristic Indicating an Early Reaction)

Check processing concerning each of Slow Reaction, Start Angle, and Early %, which are the characteristics indicating an early reaction, is explained below.

<Slow Reaction Check>

Slow Reaction check is check processing of detecting a reaction speed abnormality. Usually, an amount of change of an optical detection value is extremely small until a time point when a reagent is added to plasma, reaction advances, and fibrin is about to be formed. However, a sudden optical change is caused in a short time as the fibrin formation advances. Therefore, if a checkpoint is provided in a position of a specific amount of change between a start of occurrence of the optical change by the fibrin formation and a coagulation end level and reaction speed at the checkpoint is checked, it is possible to check presence or absence of a characteristic of an early reaction.

The reaction speed may be obtained by calculating an amount of change of the optical detection value per unit time at the checkpoint. Alternatively, a fixed range may be set around the checkpoint and a time required for causing an optical change within the range may be calculated. When a threshold is provided for the reaction speed and the reaction speed is smaller than the threshold, this means that a characteristic of a "reaction speed abnormality" is detected. Note that, for example, the threshold can be experimentally or empirically set.

Figure 6:
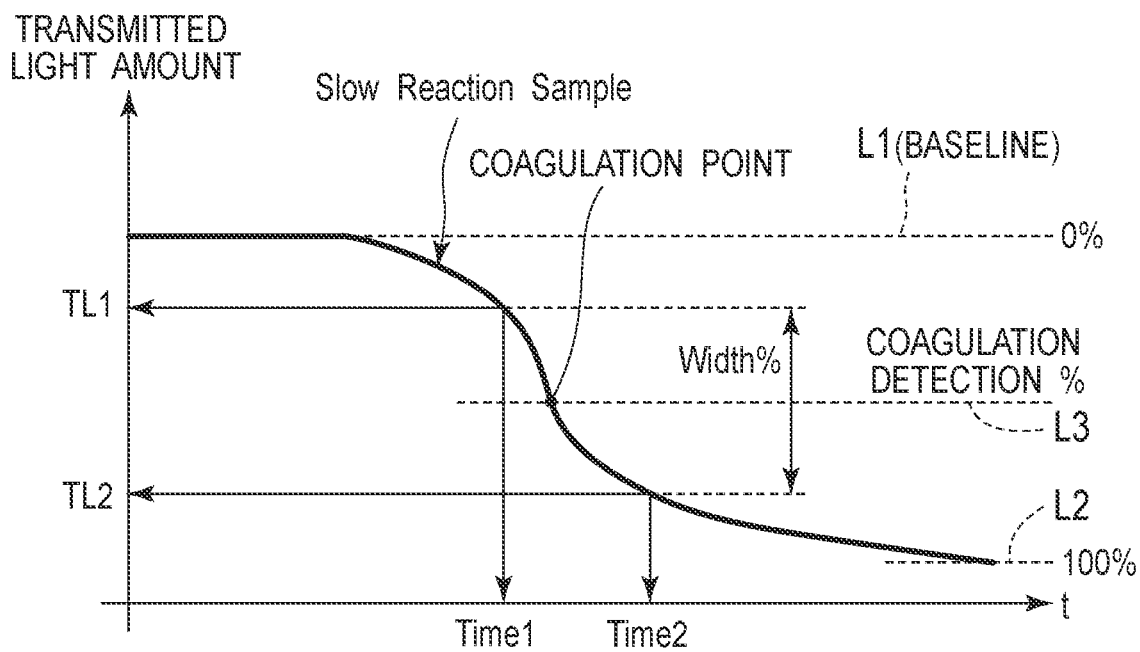
FIG. 6 is a diagram illustrating an overview of a Slow Reaction check.

FIG. 6 is a diagram for explaining an overview of the Slow Reaction check. For example, as illustrated in FIG. 6, the ERE flag is set when a reaction time (Time2−Time1) in a Width % section centering on the coagulation detection % is longer than Max Time. The coagulation detection % may be, for example, 50%. The Width % may be, for example, 12%. The Max time may be, for example, 8 seconds. The ERE flag may be set when a condition that the reaction time (Time2−Time1) is longer than the Max Time is satisfied and a point where the reaction speed ratio exceeds a reference ratio Ratio is absent before the coagulation time.

Compared with a reaction time required for a transmitted light amount change in the Width % section by a normal blood sample, a reaction time required for a transmitted light amount change in the Width % section by an abnormal blood is long. Therefore, if the Max time used as a threshold is set in advance, it is possible to determine that an ERE occurs when Time2−Time1>Max Time is satisfied. Note that the Max Time can be experimentally or empirically determined.

<Start Angle Check>

The optical detection value hardly changes in an initial time period (for example, approximately 20 seconds in APTT) in a normal coagulation curve. Therefore, it is possible to determine presence or absence of a characteristic of an early reaction by setting specific two times as checkpoints at an early stage of the coagulation curve and calculating an amount of change of the optical detection value between the checkpoints.

A threshold for the Start Angle check is set in advance. When the amount of change of the optical detection value between the two checkpoints exceeds the threshold, it is detected that there is a characteristic of an early reaction. Further, a threshold is also provided for an amount of change of the optical detection value from the baseline to the coagulation reaction stop point. When the amount of change is smaller than the threshold, it is possible to consider that a measurement error of the coagulation time occurs and display an error flag without displaying the coagulation time. When the amount of change is equal to or larger than the threshold, it is possible to display the error flag and indicate that the measurement error occurs and then display the coagulation time.

FIG. 7 is a diagram for explaining an overview of the Start Angle check. For example, as illustrated in FIG. 7, a first time point (1st Check Time in the figure) and a second time point (2nd Check Time in the figure) are set in advance in an initial time period (approximately 20 seconds in APTT) in the coagulation curve. A region between 1st Check Time and 2nd Check Time is set as a check region. The first time checkpoint is, for example, four seconds after a start time point of the coagulation curve. The second time checkpoint is, for example, eight seconds after the start time point of the coagulation curve.

Subsequently, a transmitted light change amount dH in the check region is calculated. The transmitted light change amount dH is obtained by dH2−dH1. The transmitted light change amount dH of an abnormal sample is large compared with a transmitted light change amount of a normal sample. Therefore, the threshold Delta is set. When a difference between dH1 and dH2: dH2−dH1≥Delta [level] is satisfied, the ERE flag is set.

A threshold (dH Limit) is set for the transmitted light change amount dH from the baseline L1 to the coagulation reaction stop point. When dH2−dH1≥Delta and dH≤Limit (hereinafter described as "Start Angle 1"), considering that an early reaction is seen and a sufficient optical change amount dH by fibrin formation absent, it is determined that a measurement error occurs and the ERE flag is displayed without displaying the coagulation time. When dH2−dH1≥Delta and dH>dH Limit (hereinafter described as "Start Angle 2"), although an early reaction is seen, it is determined that a sufficient optical change amount dH is present, an error flag is displayed to indicate that a measurement error occurs and then the coagulation time is displayed.

<Early % Check>

In a normal blood sample, it takes a relatively long time until an optical change by fibrin formation is caused. On the other hand, in a blood sample in which an optical change is gradually caused, the optical change occurs immediately after a reagent is added to plasma or in a relatively early time. Therefore, it is possible to detect an abnormality by setting a position of a specific optical detection value as a checkpoint (a third value), calculating a time to reach the checkpoint, and comparing the time with a second reference time (Limit) set in advance.

FIG. 8 is a diagram for explaining an overview of the Early % check. For example, as illustrated in FIG. 8, a Check Point is set in advance in a position of a specific transmitted light amount. The Early % check is a check for checking whether a time when a transmitted light amount starts to change is too early. Therefore, it is desirable to set the Check Point in a position where the transmitted light amount starts to change in the coagulation curve. Subsequently, a time required for a change to the Check Point is calculated. As the Check Point, for example, when the baseline L1 is set to 0%, the third value may be set in a position of 6%. Compared with a time required by the transmitted light amount to change to the third value in a normal sample, a time required by the transmitted light amount to change to the third value in an abnormal sample is short. Therefore, the second reference time (Limit) is set in advance. When a time required by the transmitted light amount to change to the third value is shorter than the second reference time (Limit), it is determined that the time when the transmitted light amount starts to change is too early. The ERE flag is set and displayed on the display unit 33c. The second reference time (Limit) may be set to, for example, 16.8 seconds.

(Second Check Processing)

The analysis controller 33a performs the second check processing concerning data in which the characteristic indicating the early reaction is detected in step S241 and the ERE flag is set in step S242.

Figure 9:
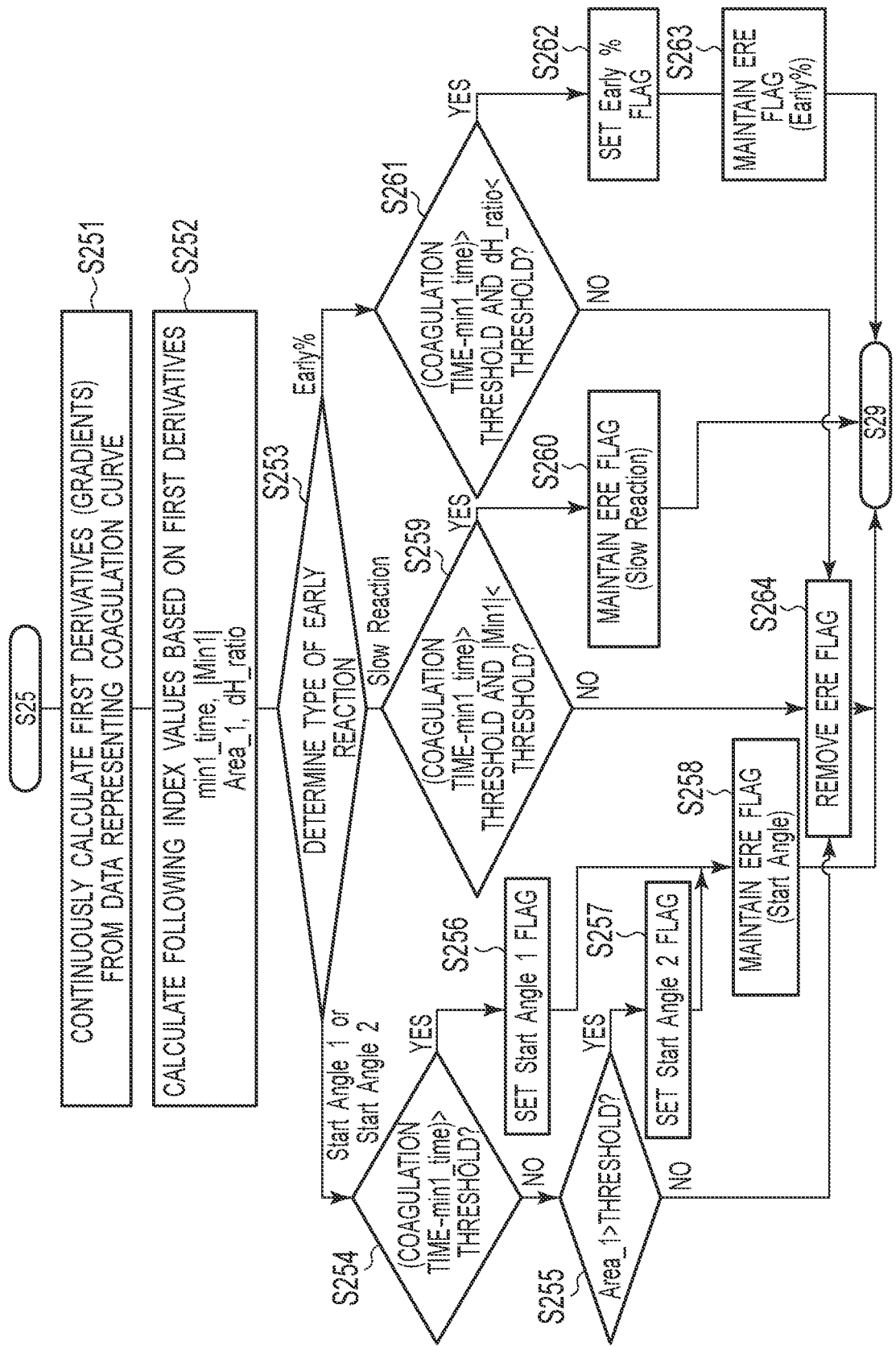
FIG. 9 is a flow diagram illustrating an example of a flow of second check processing.
Figure 10:
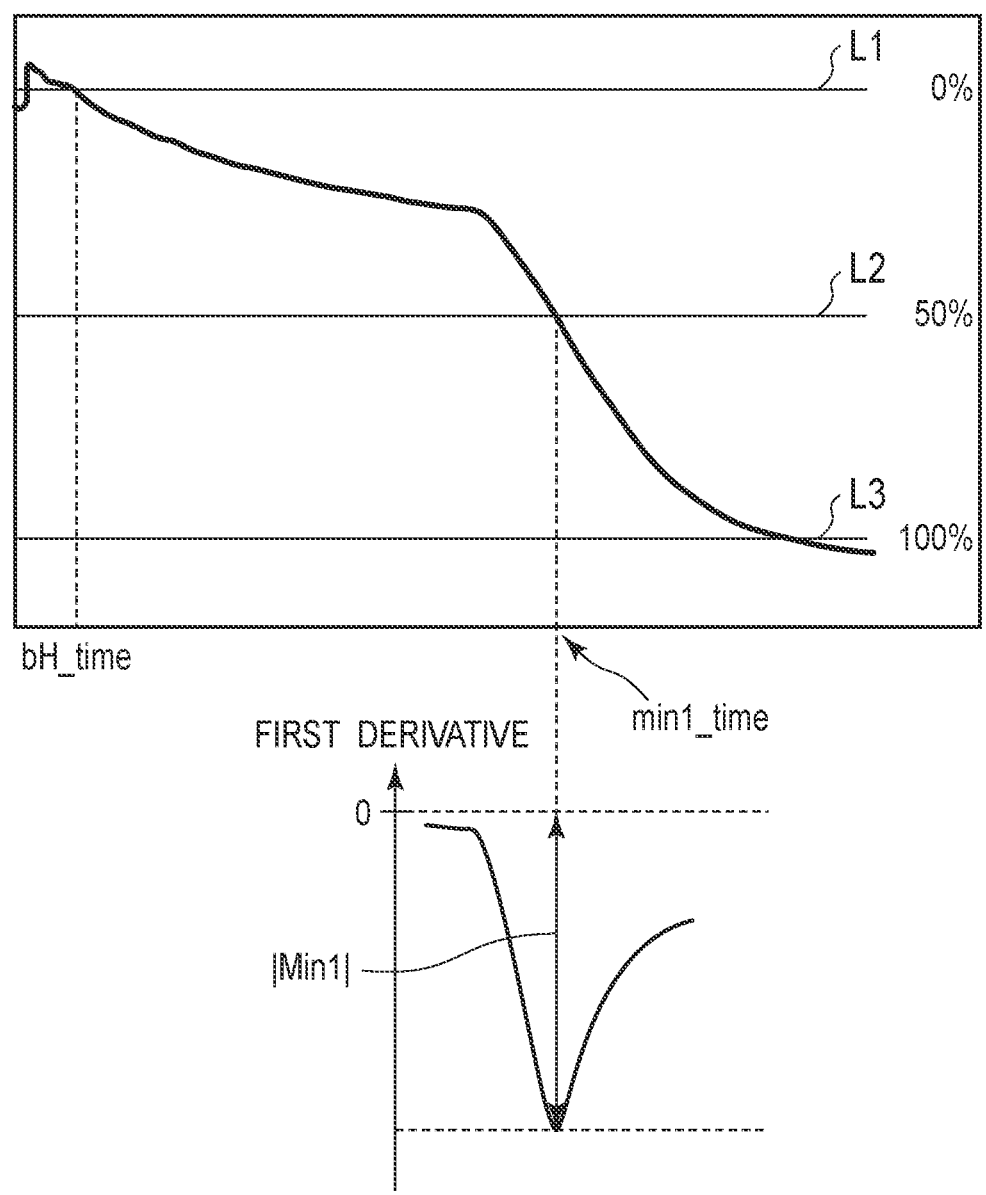
FIG. 10 is a diagram illustrating an index value.
Figure 11:
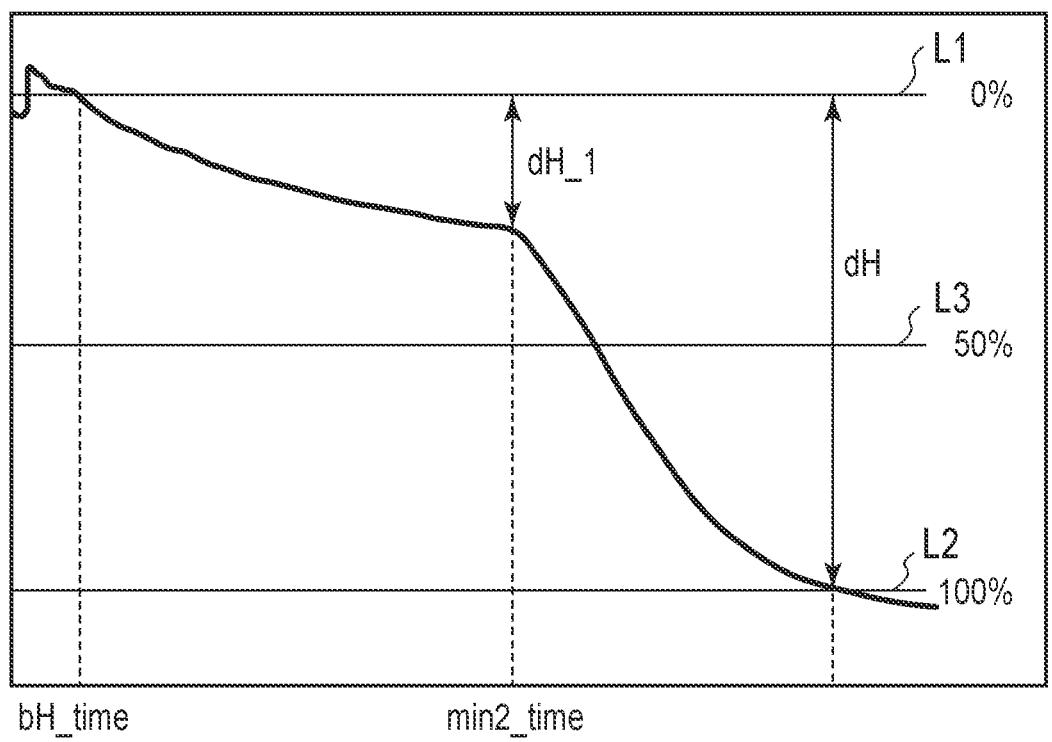
FIG. 11 is a diagram illustrating an index value.
Figure 12:
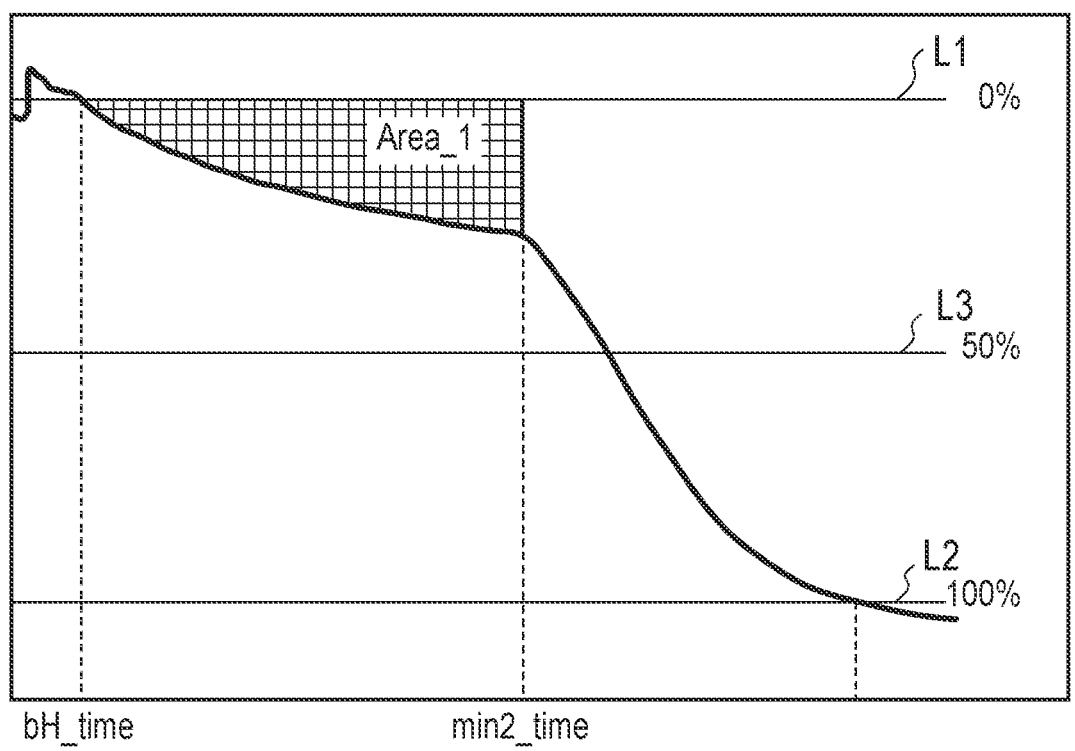
FIG. 12 is a diagram illustrating an index value.

The second check processing (step S25 in FIG. 3) is explained with reference to FIG. 9 and FIGS. 10 to 13. FIG. 9 is a flowchart illustrating an example of a flow of the second check processing. FIGS. 10 to 12 are diagrams for explaining an index value. FIG. 13 is a diagram illustrating an example of a threshold set for each index value used in the second check processing.

After step S24 in FIG. 3, in step S251, the analysis controller 33a continuously calculates first derivatives from the data representing the coagulation curve. The calculated first derivatives are values indicating gradients at points in time in the coagulation curve. Note that, in step S251, the analysis controller 33a may calculate gradients at the points in time in the coagulation curve based on linear regression in a predetermined time.

Subsequently, in step S252, the analysis controller 33a calculates the following index values based on the calculated first derivatives. Step S252 corresponds to step S2 in FIG. 2.

min1_time: In a coagulation curve illustrated in FIG. 10, a time from a first time point when a reagent is added until a second time point when a minimum value of a first derivative calculated concerning the coagulation curve is given.

|Min1|: In the coagulation curve illustrated in FIG. 10, the absolute value of the minimum value of the first derivative calculated concerning the coagulation curve.

dH_ratio: In a coagulation curve illustrated in FIG. 11, a ratio of a difference between an optical detection value at a fourth time point (min2_time) when a minimum value of a second derivative calculated concerning the coagulation curve is given and an optical detection value at a third time point (bH_time) when a predetermined time elapses from the first time point when the reagent is added and a difference between the optical direction value at a fifth time point (a coagulation reaction stop point) when a coagulation reaction can be regarded as stopped and the optical detection value at the third time point. Note that a transmitted light amount at bH_time may be the same as the transmitted light amount indicated by the baseline L1. bH_time can be set as, for example, 7.7 seconds.

Area_1: In a coagulation curve illustrated in FIG. 12, an integral value of a difference between the optical detection value in a period from the third time point (bH_time) when the predetermined time elapses from the first time point when the reagent is added until the fourth time point (min2_time) when the minimum value of the second derivative calculated concerning the coagulation curve is given and the optical detection value at the third time point.

These index values are index values selected as values directly indicating characteristics of the shape of the coagulation curve. In the second check processing, by adopting an index value selected from the group including of these index values, even if an early reaction is detected, it is possible to accurately determine whether a coagulation time is calculated with the early reaction misrecognized as a coagulation reaction.

In step S253, the analysis controller 33a determines a type of the early reaction based on the characteristic indicating the early reaction detected in the first check processing. The analysis controller 33a may determine a type of the early reaction based on, for example, which of the Slow Reaction flag, the Start Angle flag, and the Early % flag the flag set in step S242 is.

As processing in step S253 and subsequent steps, different processing is performed for each type of the early reaction.

<When the Early Reaction is Determined as Slow Reaction>

In step S259, the analysis controller 33a compares a difference between the coagulation time calculated in step S23 and min1_time with a predetermined threshold illustrated in FIG. 13. The analysis controller 33a compares |Min1| with a predetermined threshold illustrated in FIG. 13. The analysis controller 33a determines whether the ERE flag is removed or maintained based on a result of the comparison. When the difference between the coagulation time and min1_time is, for example, larger than 10 seconds and |Min1| is, for example, smaller than 0.1 (YES in step S259), the analysis controller 33a maintains the ERE flag (and the Slow Reaction flag) (step S260) and proceeds to step S29. On the other hand, when the difference between the coagulation time and min1_time is, for example, equal to or smaller than 10 seconds or |Min1| is, for example, equal to or larger than 0.1 (NO in step S259), the analysis controller 33a removes the ERE flag (and the Slow Reaction flag) (step S264) and proceeds to step S29.

<When the Early Reaction is Determined as Start Angle>

In step S254, the analysis controller 33a compares the difference between the coagulation time calculated in step S23 and min1_time with the predetermined threshold illustrated in FIG. 13. The analysis controller 33a determines whether the ERE flag is removed or maintained based on a result of the comparison. When the difference between the coagulation time and min1_time is larger than the predetermined threshold (YES in step S254), the analysis controller 33a sets a Start Angle 1 flag (step S256), maintains the ERE flag (step S258), and proceeds to step S29. On the other hand, when the difference between the coagulation time and min1_time is equal to or smaller than the predetermined threshold (NO in step S254), the analysis controller 33a proceeds to step S255.

In step S255, the analysis controller 33a compares Area_1 with a predetermined threshold illustrated in FIG. 13. When the Area_1 is, for example, larger than 1 (YES in step S255), the analysis controller 33a sets a Start Angle 2 flag (step S257), maintains the ERE flag (step S258), and proceeds to step S29. On the other hand, when Area_1 is, for example, equal to or smaller than 1 (NO in step S255), the analysis controller 33a removes the ERE flag (and the Start Angle flag) (step S264) and proceeds to step S29.

<When the Early Reaction is Determined as Early %>

In step S261, the analysis controller 33a compares the difference between the coagulation time calculated in step S23 and min1_time with the predetermined threshold illustrated in FIG. 13. The analysis controller 33a determines whether the ERE flag is removed or maintained based on a result of the comparison. When the difference between the coagulation time and min1_time is larger than the predetermined threshold and dH_ratio is, for example, smaller than 0.2 (YES in step S261), the analysis controller 33a sets the Early % flag (step S262), maintains the ERE flag (step S263), and proceeds to step S29. On the other hand, when the difference between the coagulation time and min1_time is equal to or smaller than the predetermined threshold or dH_ratio is, for example, equal to or larger than 0.2 (NO in step S261), the analysis controller 33a removes the ERE flag (step S264) and proceeds to step S29.

Note that the predetermined thresholds illustrated in FIG. 13 are values set such that an analysis result (for example, a calculated coagulation time) in a blood coagulation analysis has reliability of a degree applicable to a clinical test and a diagnosis. In other words, the predetermined thresholds are values set such that, when an early reaction is detected in a coagulation curve, a determination result not greatly contradictory to a determination result obtained when a specialist of the blood coagulation analysis views and confirms the coagulation curve is output. By adopting such a configuration, even if an early reaction is detected in a coagulation curve used to calculate the coagulation time, it is possible to appropriately remove the ERE flag when there is no problem in reliability of the calculated coagulation time.

Second Embodiment

A second embodiment is explained below.

Figure 14:
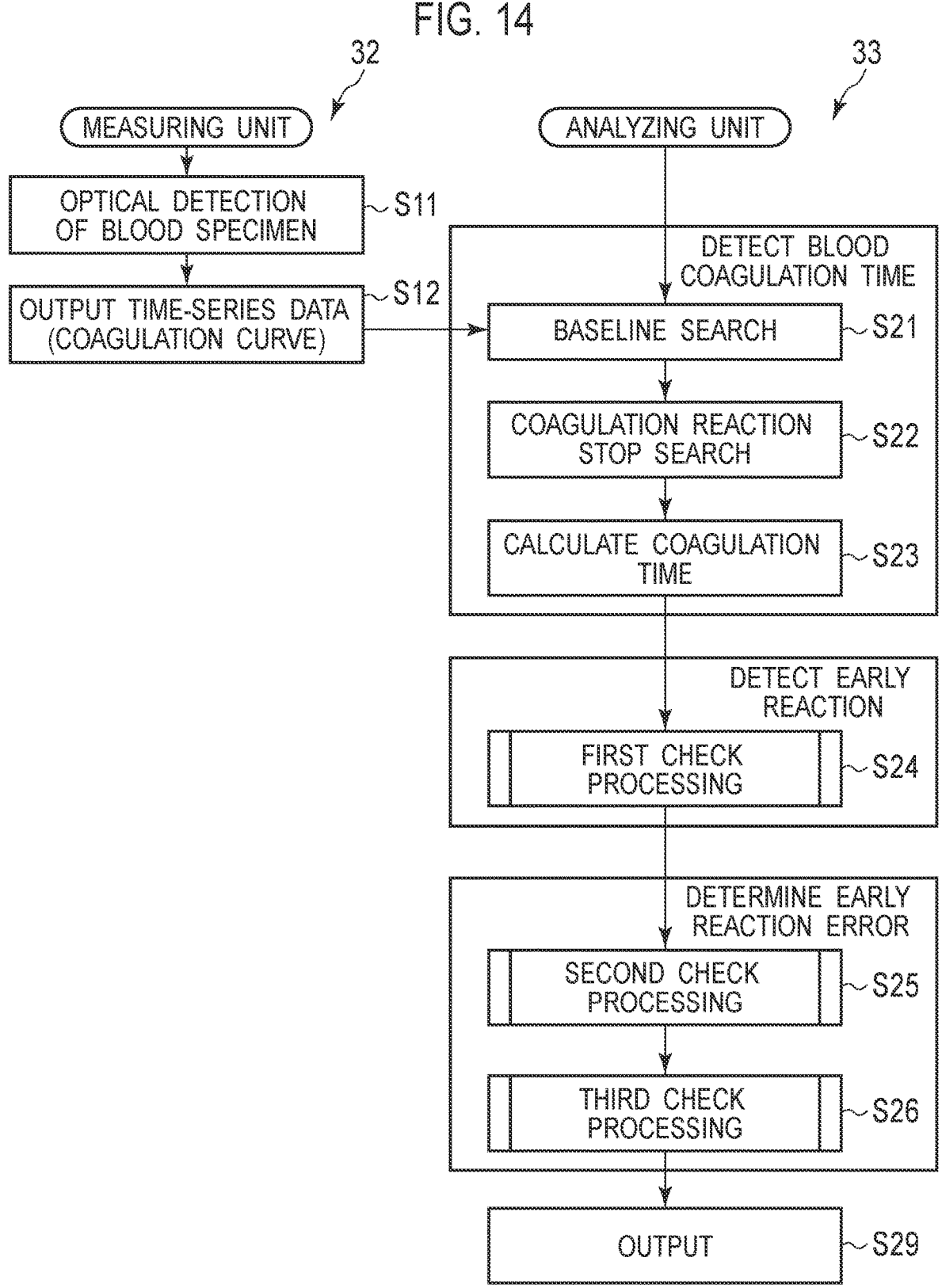
FIG. 14 is a flow diagram illustrating an example of a flow of processing of a blood coagulation analyzing method.

FIG. 14 is a flowchart illustrating another example of the flow of the processing of the blood coagulation analyzing method. As illustrated in FIG. 14, the third check processing (step S27) may be performed following the second check processing in step S25. Note that the third check processing is not limited to be performed after the second check processing. For example, when characteristics of the early reaction, that is, Start angle and Early % are detected in step S241 in FIG. 5, the third check processing may be performed instead of the second check processing.

Figure 15:
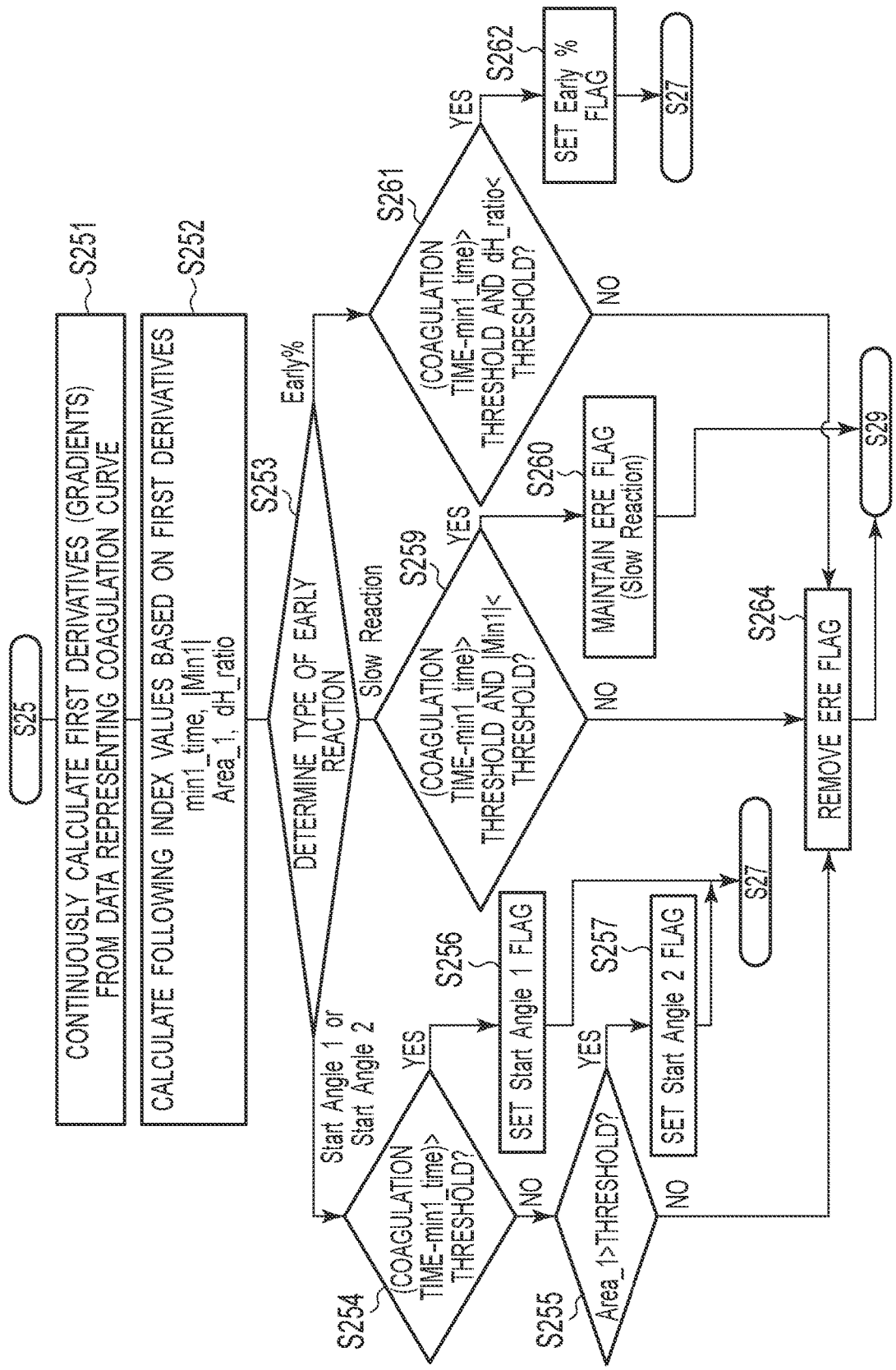
FIG. 15 is a flow diagram illustrating an example of a flow of second check processing.

A configuration in which the third check processing is performed after the second check processing is explained with reference to FIG. 15. FIG. 15 is a flowchart illustrating another example of the flow of the second check processing. Note that, for convenience of explanation, members having the same functions as the functions of the members explained above in embodiments are denoted by the same reference numerals and signs and explanation of the members is not repeated.

In FIG. 9, the ERE flag is maintained in step S256, step S257, and step S262. However, in the example illustrated in FIG. 15, it is further determined with the third check processing whether the ERE flag is maintained.

(Third Check Processing)

Figure 16:
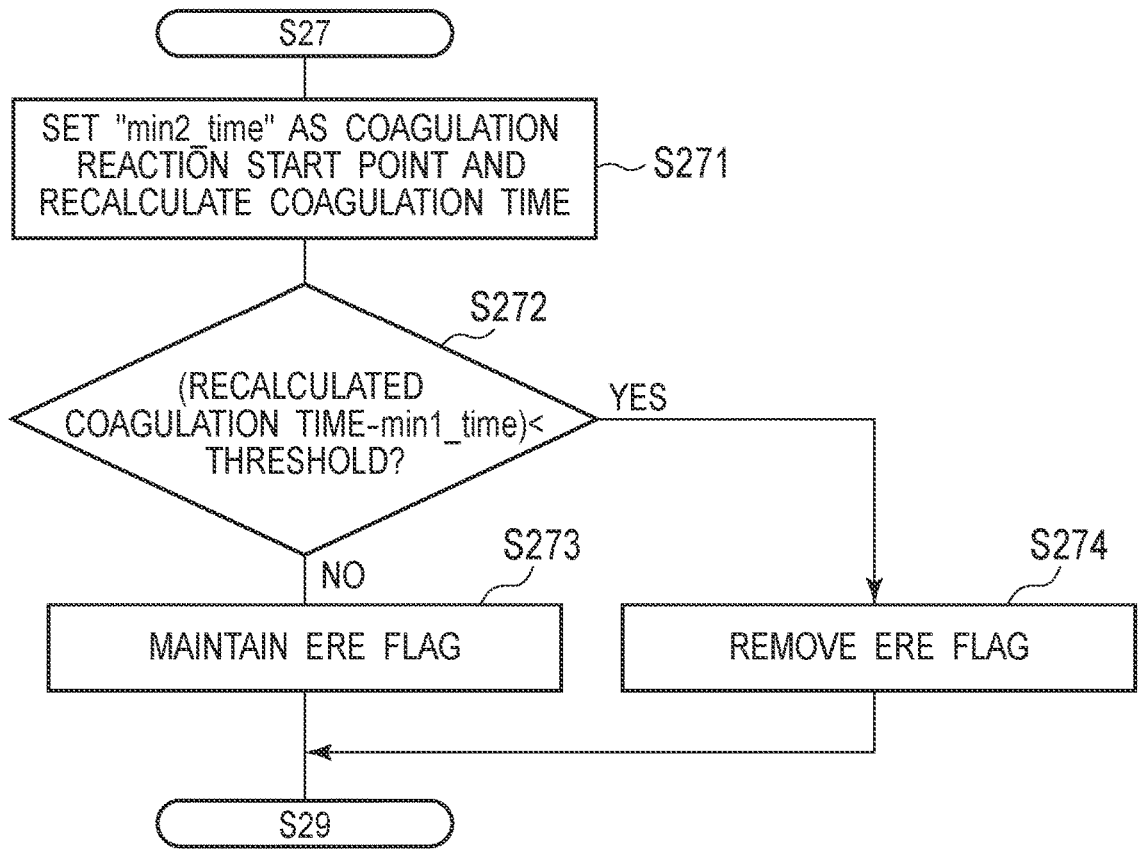
FIG. 16 is a flow diagram illustrating an example of a flow of third check processing.

The third check processing (step S27 in FIG. 14) is explained with reference to FIG. 16 and FIGS. 17 and 18. FIG. 16 is a flowchart illustrating an example of the flow of the third check processing.

In step S271, the analysis controller 33a sets, as a coagulation reaction start point, the fourth time point (min2_time in the coagulation curve illustrated in FIG. 11) when the minimum value of the secondary differential of the coagulation curve is given and recalculates a coagulation time.

Figure 17:
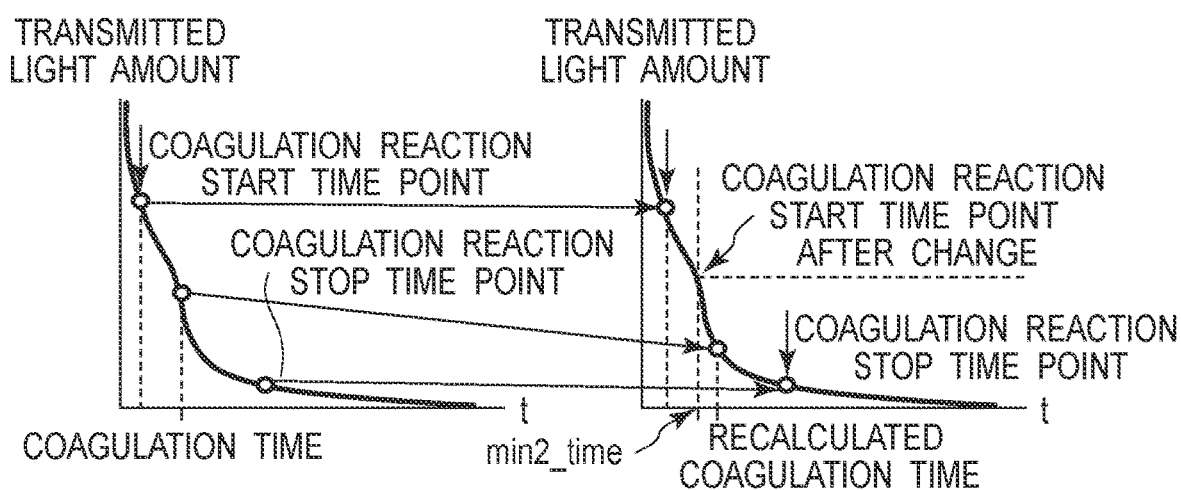
FIG. 17 is a diagram illustrating recalculation of a coagulation time.

FIG. 17 is a diagram for explaining the recalculation of a coagulation time. When calculating a coagulation time in step S23, the analysis controller 33a adopts a reaction start time point illustrated on a coagulation curve illustrated on the left side of FIG. 17 and calculates a coagulation time. On the other hand, in step S271, as illustrated on the right side in FIG. 17, the analysis controller 33a calculates a coagulation time with the reaction start time point changed to the fourth time point when the minimum value of the second derivative calculated concerning the coagulation curve is given.

Subsequently, in step S272, the analysis controller 33a compares a difference between the coagulation time recalculated in step S271 and min1_time with a predetermined threshold illustrated in FIG. 18. The analysis controller 33a determines whether the ERE flag is removed or maintained based on a result of the comparison.

When the difference between the recalculated coagulation time and min1_time is equal to or larger than the predetermined threshold (NO in step S272), the analysis controller 33a maintains the ERE flag (step S273) and proceeds to step S29. On the other hand, when the difference between the recalculated coagulation time and min1_time is smaller than the predetermined threshold (YES in step S272), the analysis controller 33a removes the ERE flag (step S274) and proceeds to step S29.

Figures 18, 19:
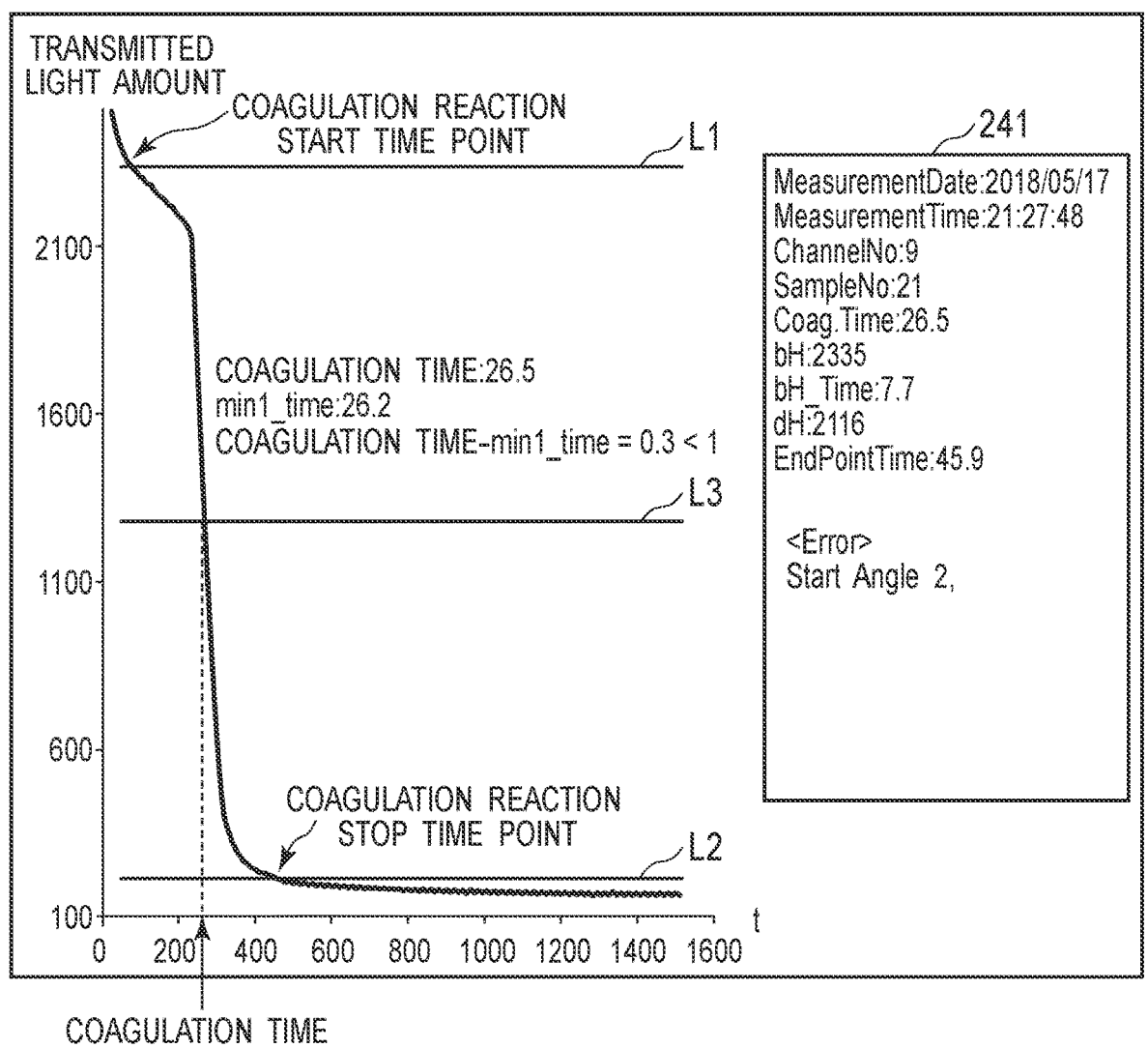
FIG. 18 is a diagram illustrating an example of a threshold that can be applied in third check processing.
FIG. 19 is a diagram illustrating an example of an APTT coagulation curve in which an ERE flag is removed by second check processing.

Note that the predetermined threshold illustrated in FIG. 18 is a value set such that an analysis result (for example, a calculated coagulation time) in a blood coagulation analysis has reliability of a degree applicable to a clinical test and a diagnosis. In other words, the predetermined threshold is a value set such that, when an early reaction is detected in a coagulation curve, a determination result not greatly contradictory to a determination result obtained when a specialist of the blood coagulation analysis views and confirms the coagulation curve is output.

The fourth time point when a minimum value of second derivative calculated concerning a large number of coagulation curves in which an early reaction is detected is given is a time point when the influence due to the early reaction may be regarded as being substantially eliminated. With the configuration explained above, it is possible to recalculate a coagulation time with high reliability from a coagulation curve having a shape affected by the early reaction.

(Output of the Coagulation Time)

When the ERE flag is removed, in step S29, the coagulation time calculated in step S23 and step S271 is displayed on the display unit 33c without display of an error flag. When the ERE flag is set, the error flag is displayed. When the error flag is displayed, only the error flag may be displayed without displaying the coagulation time or the error flag may be displayed together with the coagulation time. In this way, an output form of the coagulation time can be varied according to the ERE flag.

When the ERE flag is set, the display of the error flag is added to the display of the coagulation time. The display indicating the error flag may be "*". The error flag "*" indicates that, for example, reliability of the displayed coagulation time is low.

(Determination Example: An Example in which the ERE Flag is Removed)

Figure 20:
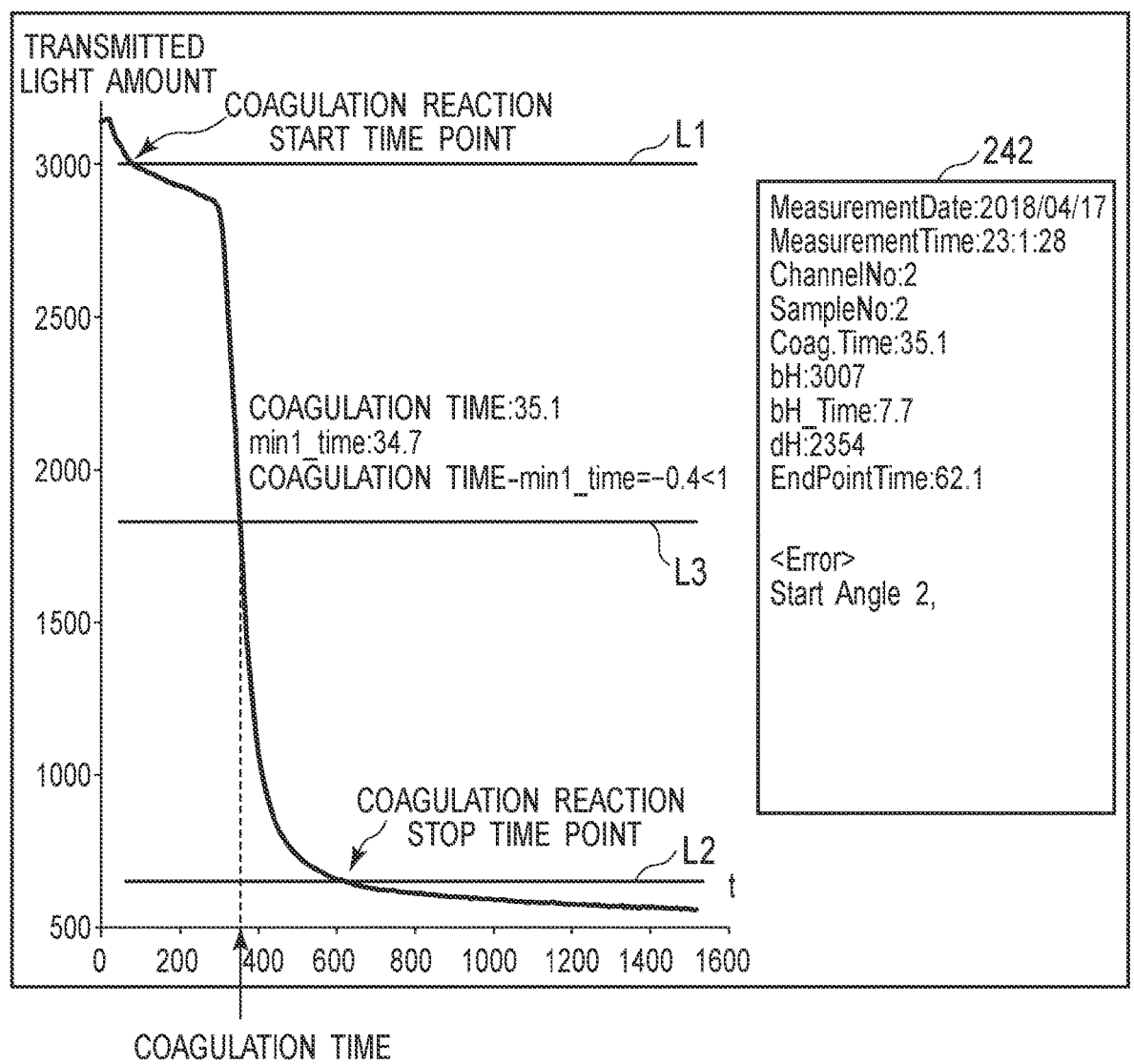
FIG. 20 is a diagram illustrating an example of an APTT coagulation curve in which an ERE flag is removed by second check processing.

FIGS. 19 and 20 illustrate examples of APTT coagulation curves in which the ERE flag is removed by the second check processing in step S25. As illustrated in a region 241 in FIG. 19 and a region 242 in FIG. 20, the ERE flag is set by a Start Angle 2 check.

A coagulation time calculated from the APTT coagulation curve illustrated in FIG. 19 is 26.5 seconds. The index value min1_time calculated in step S2 is 26.2 seconds. A difference between the coagulation time and min1_time is 0.3. This value is equal to or smaller than 1 (see FIG. 13), which is the predetermined value (corresponding to NO in step S254 in FIG. 15). Note that, since the ERE flag is set in the APTT coagulation curve illustrated in FIG. 19 by the Start Angle 2 check, it is determined NO in step S255 in FIG. 15 as well. Therefore, the analysis controller 33*a* proceeds to step S264 in FIG. 15 and removes the ERE flag.

A coagulation time calculated from the APTT coagulation curve illustrated in FIG. 20 is 34.7 seconds. The index value min1_time calculated in step S2 is 35.1 seconds. A difference between the coagulation time and min1_time is 0.4. This value is equal to or smaller than 1 (see FIG. 13), which is the predetermined threshold (corresponding to NO in step S254 in FIG. 15). Note that, since the ERE flag is set in the APTT coagulation curve illustrated in FIG. 20 by the Start Angle 2 check, it is determined NO in step S255 in FIG. 15 as well. Therefore, the analysis controller 33*a* proceeds to step S264 in FIG. 15 and removes the ERE flag.

(Determination Example: An Example in which the ERE Flag is Maintained)

Figure 21:
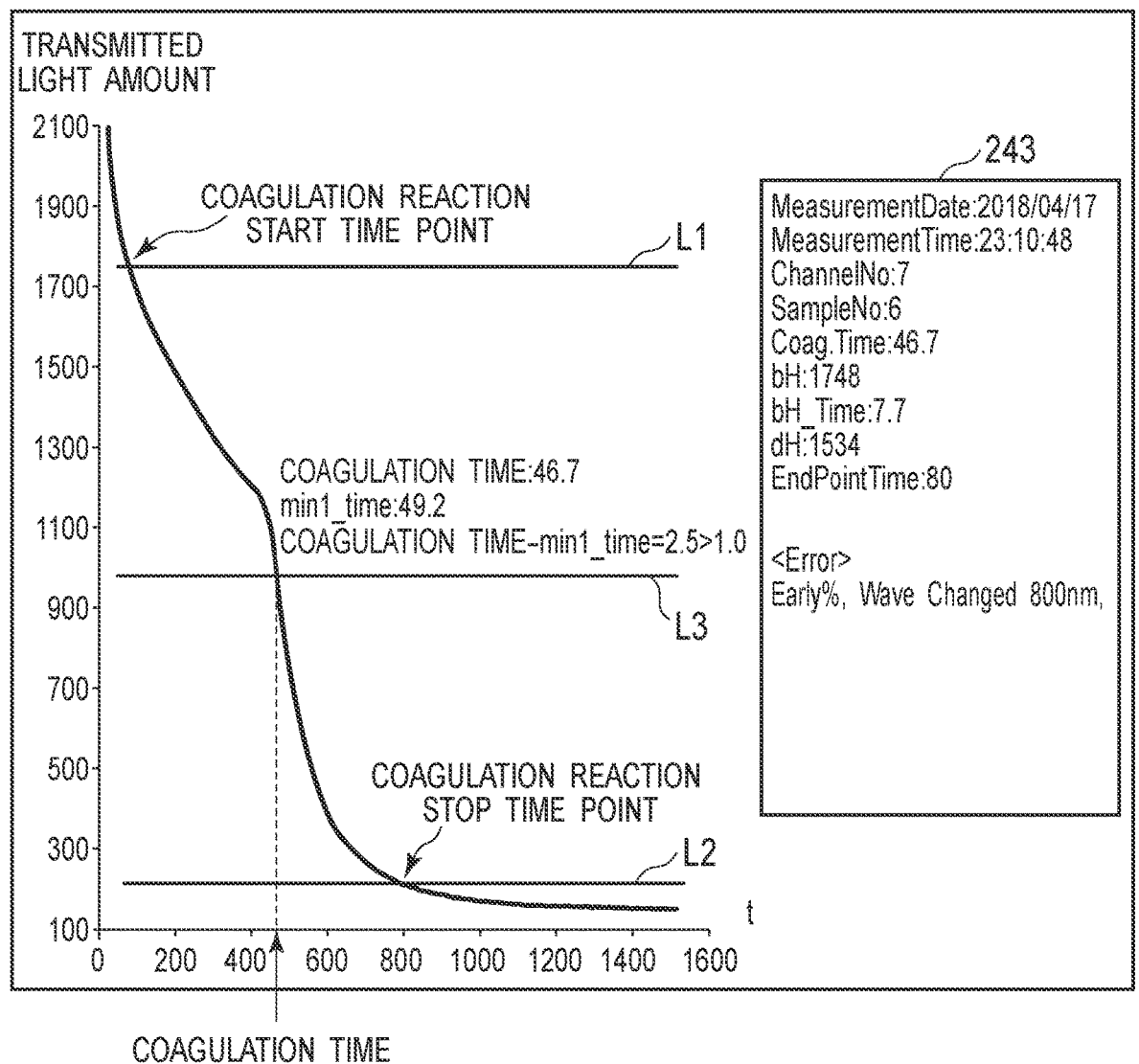
FIG. 21 is a diagram illustrating an example of an APTT coagulation curve in which an ERE flag is removed by second check processing.
Figure 22:
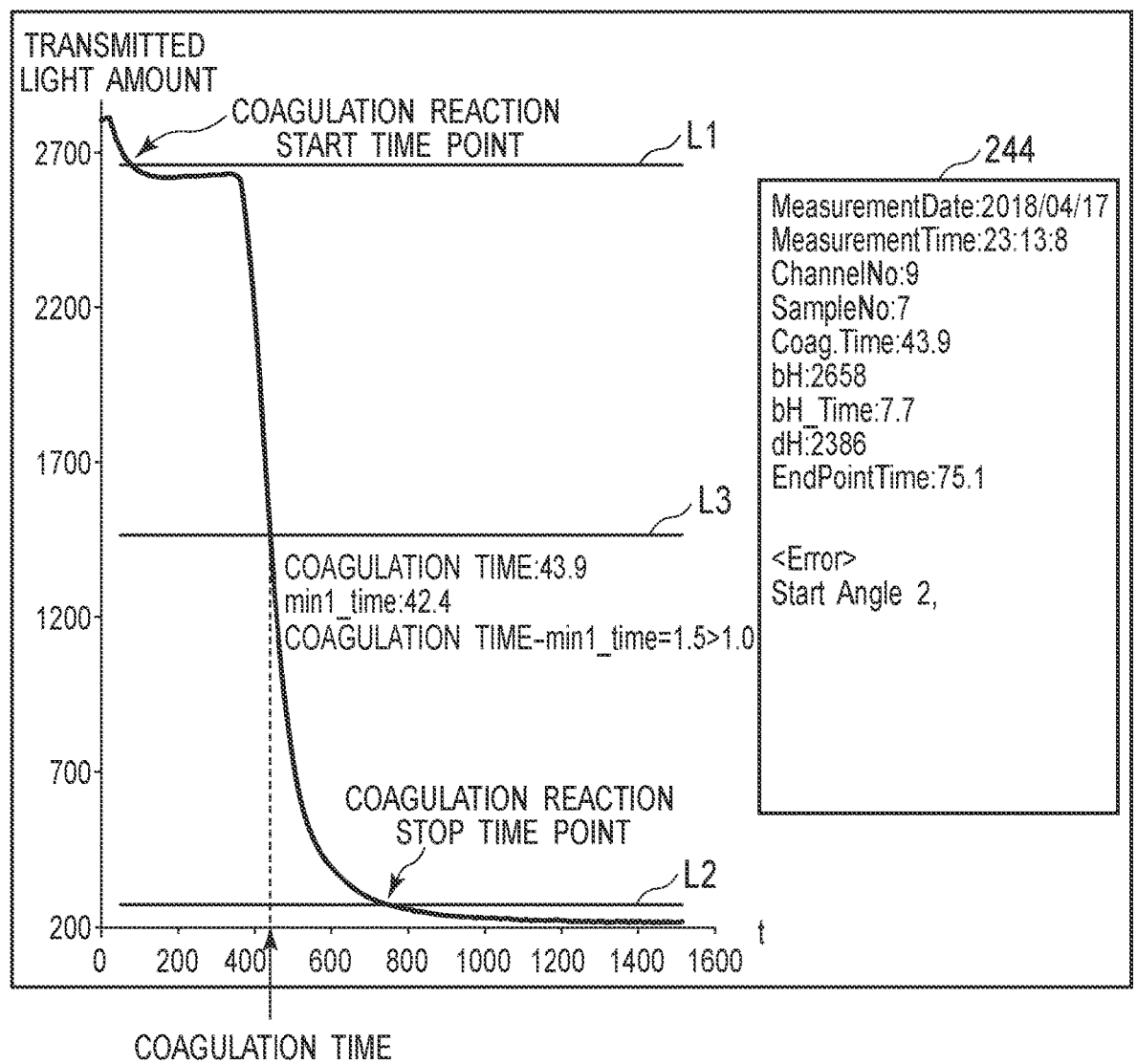
FIG. 22 is a diagram illustrating an example of an APTT coagulation curve in which an ERE flag is removed by second check processing.

FIGS. 21 and 22 illustrate examples of APTT coagulation curves in which the ERE flag is maintained by the second check processing in step S25. In the example illustrated in FIG. 21, as illustrated in a region 243, the ERE flag is set by the Early % check. On the other hand, in the example illustrated in FIG. 22, as illustrated in a region 244, the ERE flag is set by a Start Angle 1 check.

A coagulation time calculated from the APTT coagulation curve illustrated in FIG. 21 is 46.7 seconds. The index value min1_time calculated in step S2 is 49.2 seconds. A difference between the coagulation time and min1_time is 2.5. This value is larger than 1 (see FIG. 13), which is the predetermined threshold, and, although not illustrated in the figure, the index value dH_ratio is smaller than 0.2 (see FIG. 13), which is the predetermined threshold (corresponding to YES in step S261 in FIG. 15). Therefore, the analysis controller 33*a* proceeds to step S263 through step S262 in FIG. 15 and maintains the ERE flag.

A coagulation time calculated from the APTT coagulation curve illustrated in FIG. 22 is 43.9 seconds. The index value min1_time calculated in step S2 is 42.4 seconds. A difference between the coagulation time and min1_time is 1.5. This value is larger than 1 (see FIG. 13), which is the predetermined threshold (corresponding to YES in step S254 in FIG. 15). Therefore, the analysis controller 33*a* proceeds to step S258 through step S256 in FIG. 15 and maintains the ERE flag.

(Determination Example: An Example in which the Third Check Processing is Applied)

Figure 23:
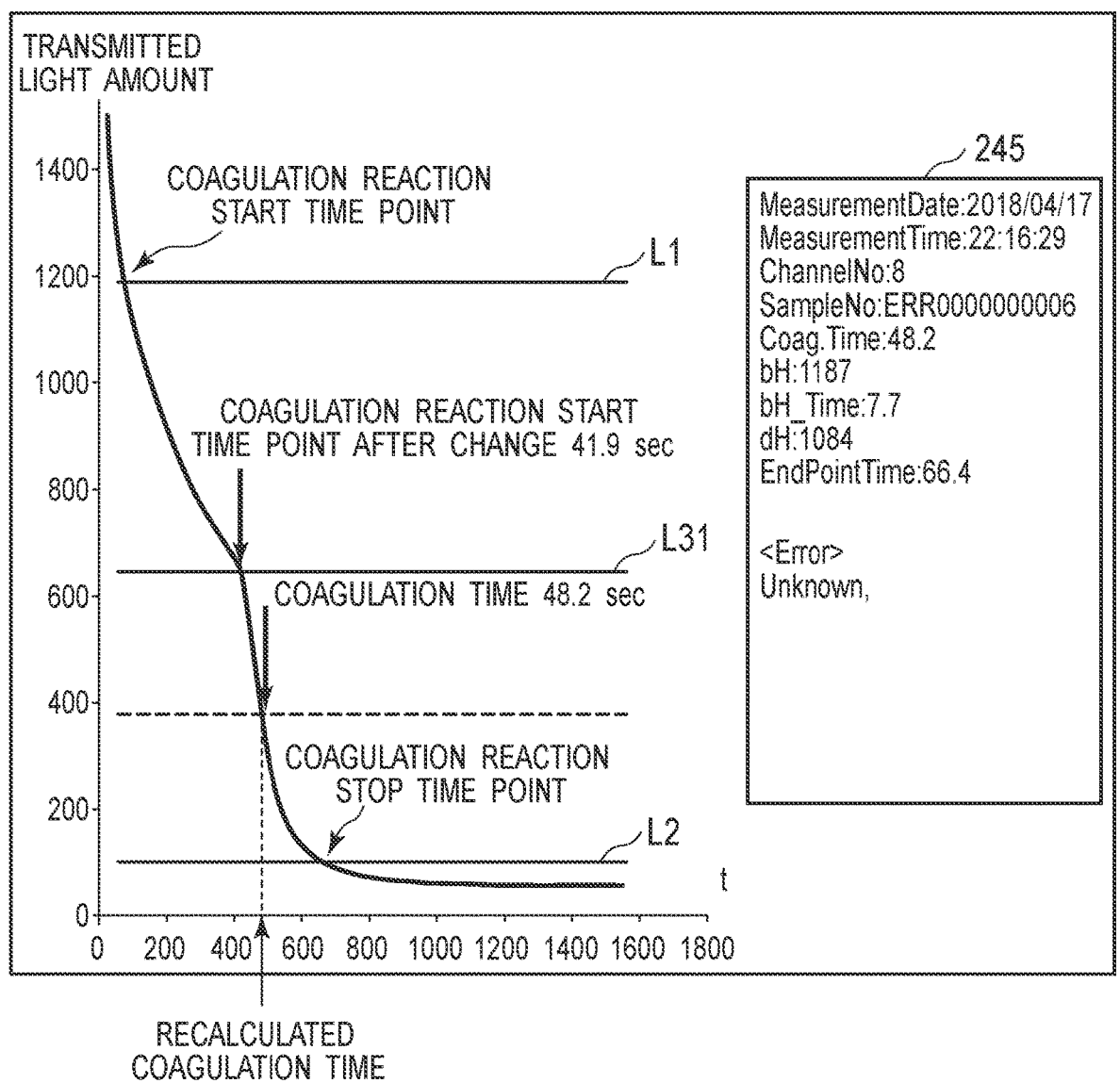
FIG. 23 is a diagram illustrating an example of an APTT coagulation curve to which third check processing is applied.
Figure 24:
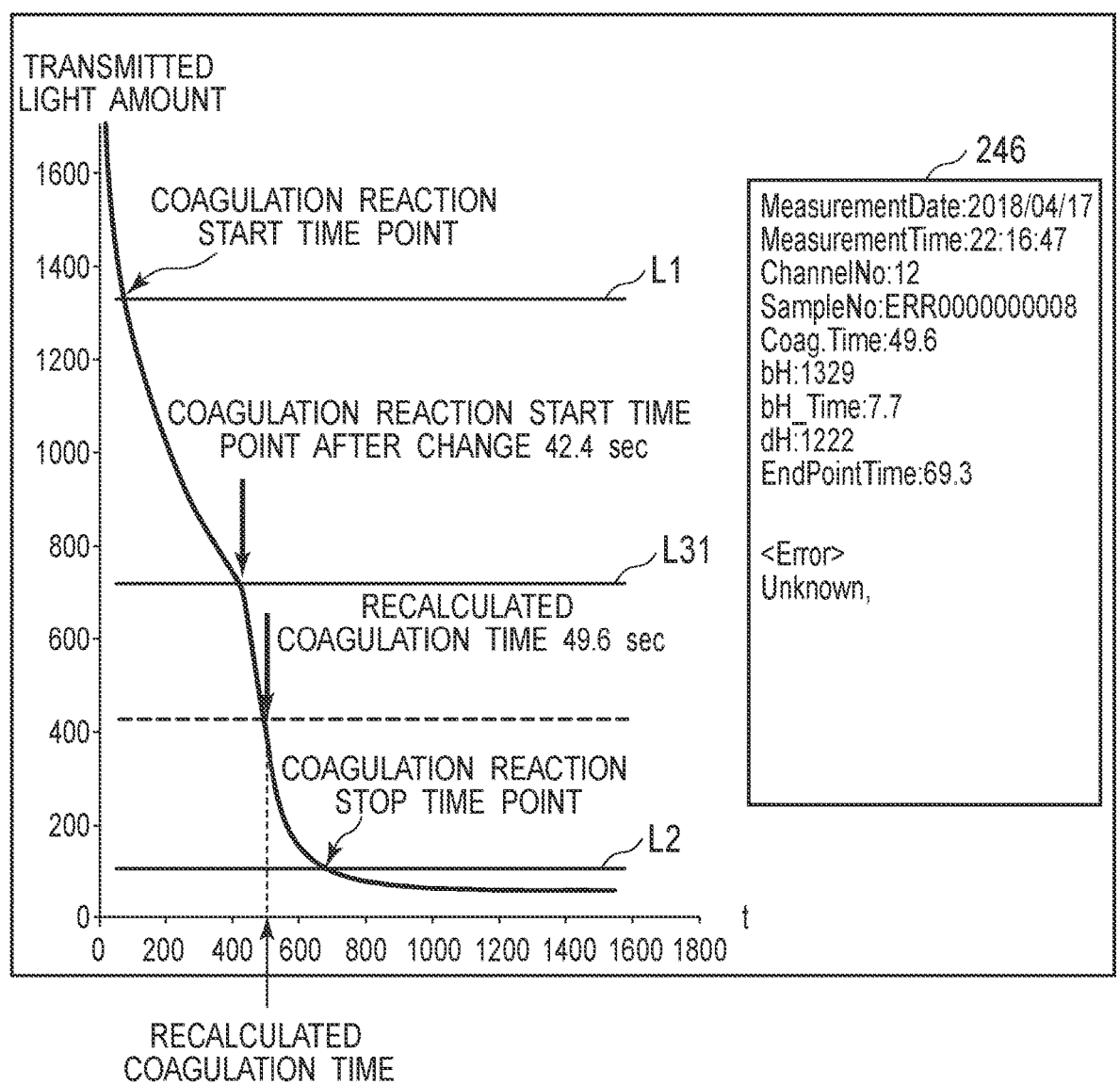
FIG. 24 is a diagram illustrating an example of an APTT coagulation curve to which third check processing is applied.

FIGS. 23 and 24 are diagrams illustrating examples of APTT coagulation curves applied with the third check processing illustrated in step S27. In the coagulation curves illustrated in FIGS. 23 and 24, the ERE flag is not removed in the second check processing as well.

The coagulation reaction start time point used when the coagulation time is calculated in step S23 is changed to a position illustrated as "a coagulation reaction start time point after change" in FIG. 23. The coagulation reaction start time point after change is a time point of 41.9 seconds. A line L31 in the figure is a line indicating a transmitted light amount at the coagulation reaction start time point after change. When the transmitted light amount of the line L31 is set to 0% and the transmitted light amount of the line L2 is set to 100%, the coagulation time is given as reading of a time axis corresponding to a position of an intersection of a line (a broken line in the figure) indicating a transmitted light amount of 50% and the coagulation curve. The coagulation time recalculated in step S271 in FIG. 16 is 48.2 seconds. A difference between the coagulation time recalculated in step S271 in FIG. 16 and min1_time is smaller than the predetermined threshold illustrated in FIG. 18. Therefore, the ERE flag is removed. Note that it is confirmed that the recalculated coagulation time is a value close to 49.2 seconds, which is a value separately manually calculated by a person who performs a blood coagulation analysis, and has certain reliability.

The same applies in the example illustrated in FIG. 24. That is, the coagulation time recalculated in step S271 in FIG. 16 is 49.6 seconds. A difference between the coagulation time recalculated in step S271 in FIG. 16 and min1_time is smaller than the predetermined threshold illustrated in FIG. 18. Therefore, the ERE flag is removed. Note that it is confirmed that the recalculated coagulation time is a value close to 52.1 seconds, which is a value separately manually calculated by a person who performs a blood coagulation analysis, and has certain reliability.

(Reduction Result of the ERE Flag)

FIGS. 25 and 26 and FIGS. 27 and 28 illustrate reduction results of the ERE flag in the case in which the blood coagulation analyzing method illustrated in FIG. 15 is applied. In FIG. 25 and FIG. 28, the numbers of each type of early reactions detected in measurement specimens analyzed in the past in cities different from each other are describe in "Current" fields. The number of maintenances of the ERE flag (for example, "Early %"), the number of removals of the ERE flag (No Error), and the number indicating results of recalculation of a coagulation time (Coag % Changed) when the blood coagulation analyzing method according to an embodiment is applied are illustrated.

In the example illustrated in FIG. 25, there are twenty-eight examples of results concerning measurement specimens in which early reactions are detect and the ERE flag is set. As a result of applying the blood coagulation analyzing method according to an embodiment, the ERE flag is maintained in one example ("Early %"), the ERE flag is removed in eighteen examples, and results of recalculation of a coagulation time are indicated in nine examples.

Results obtained by confirming effects of the second check processing and the third check processing concerning twenty-three examples separately determined by a specialist, who performs a blood coagulation analysis, that an early reaction is detected, an ERE occurs, and a calculated coagulation time is unreliable (True error) are illustrated in FIG. 26.

In ten examples among the twenty-three examples, the ERE flag is maintained even if the second check processing is performed. In one example among the ten examples in which the ERE flag is maintained by the second check processing, the ERE flag is maintained by the third check processing.

If a coagulation time determined as reliable as a result of the specialist visually observing a shape of a coagulation curve is referred to as "False Positive", a ratio of successful reduction of False Positive by the second check processing out of the examples in which the ERE flag is set is 13/23=57%. A satisfactory result is obtained. Note that, if the third check processing is performed in addition to the second check processing, the ratio of successful reduction of False Positive out of the examples in which the ERE flag is set is improved to 22/23=96%.

The same applies in the examples illustrated in FIGS. 27 and 28. A ratio of successful reduction of False Positive out of the examples in which the ERE flag is set is 44/69=64%. A satisfactory result is obtained. Note that, if the third check processing is performed in addition to the second check processing, the ratio of successful reduction of False Positive out of the examples in which the ERE flag is set is improved to 69/69=100%.

The present invention is not limited to embodiments explained above. Various changes are possible in a scope indicated by claims. Embodiments obtained by combining, as appropriate, technical means respectively disclosed in different embodiments are also included in the technical scope of the present invention.

The invention claimed is:

1. A blood coagulation analyzing method comprising:
calculating a coagulation time based on data representing a change in an optical detection value of a blood specimen added with a reagent for starting a coagulation reaction, the optical detection value representing amount of light transmitted through the blood specimen added with the reagent;
calculating an index value related to derivatives calculated concerning a coagulation curve represented by the data used in the calculating the coagulation time; and
determining whether an early reaction error has occurred based on a comparison result obtained by comparing the index value to a predetermined threshold, wherein the index value comprises at least one of:
a time period from a first time point at which the reagent is added to a second time point at which a minimum value of a first derivative calculated concerning the coagulation curve is obtained;
an absolute value of the minimum value of the first derivative calculated concerning the coagulation curve;
an integral value of a difference between: the optical detection values in a time period from a third time point at which a predetermined time elapses from the first time point to a fourth time point at which a minimum value of a second derivative calculated concerning the coagulation curve is obtained; and the optical detection value at the third time point; or
a ratio of:
the difference between the optical detection value at the fourth time point and the optical detection value at the third time point; to
a difference between an optical direction value at a fifth time point at which the coagulation reaction is regarded as stopped and the optical detection value at the third time point.

2. The blood coagulation analyzing method according to claim 1, wherein
the determining comprises determining that the early reaction error has occurred in response to a difference larger than a threshold, the difference between the coagulation time and a time period from a first time point at which the reagent is added to a second time point at which a minimum value of a first derivative calculated concerning the coagulation curve is obtained.

3. The blood coagulation analyzing method according to claim 1, further comprising detecting a characteristic indicating an early reaction in the coagulation curve, wherein
in response to detection of the characteristic indicating the early reaction, the comparison result is obtained by comparing the index value to the predetermined threshold.

4. The blood coagulation analyzing method according to claim 3, wherein the characteristic comprises at least one of:
a characteristic indicating that, in the coagulation curve, a time period of a change from a first optical detection value to a second optical detection value is longer than a first reference time;
a characteristic indicating that, in the coagulation curve, a change in the optical detection value for a predetermined period is larger than a predetermined reference value; or
a characteristic indicating that, in the coagulation curve, a time period to reach a third optical detection value is shorter than a second reference time.

5. The blood coagulation analyzing method according to claim 3, wherein
the determining is performed in response to detection of the characteristic.

6. The blood coagulation analyzing method according to claim 1, wherein the calculating the coagulation time comprises calculating the coagulation time, based on the coagulation curve, as a time in which the blood specimen reaches a coagulation point.

7. The blood coagulation analyzing method according to claim 1, wherein the calculating the coagulation time comprises:
determining a sixth time point at which an ratio based on the optical detection value is detected to be a predetermined value, the ratio of:
a difference between the optical detection value at the third time point and the optical detection value at the sixth time point, to
a difference between the optical detection value at the third time point and the optical detection value at the fifth time point; and
determining a time period from the first time point to the sixth time point as the coagulation time.

8. The blood coagulation analyzing method according to claim 1, wherein the data comprises at least optical detection values during a time period from a start of the coagulation reaction to a stop of the coagulation reaction in the blood specimen.

9. The blood coagulation analyzing method according to claim 1, further comprising:
in response to determining that the early reaction error has occurred, recalculating the coagulation time with a coagulation reaction start time point changed from a time point at which the coagulation reaction is first observed in the blood specimen.

10. The blood coagulation analyzing method according to claim 9, wherein, in the recalculating, the coagulation reaction start time point is set to a fourth time point at which a minimum value of a second derivative calculated concerning the coagulation curve is obtained.

11. The blood coagulation analyzing method according to claim 9, further comprising:
   redetermining whether the early reaction error has occurred based on a difference between the recalculated coagulation time and a time from a first time point at which the reagent is added to a second time point at which a minimum value of a first derivative calculated concerning the coagulation curve is obtained.

12. The blood coagulation analyzing method according to claim 11, further comprising displaying an error flag on a display in response to redetermining that the early reaction error has occurred.

13. The blood coagulation analyzing method according to claim 12, wherein the displaying the error flag comprising displaying the error flag with the coagulation time.

14. The blood coagulation analyzing method according to claim 1, further comprising displaying an error flag on a display in response to determining that the early reaction error has occurred.

15. The blood coagulation analyzing method according to claim 1, further comprising outputting the coagulation time in an output form depending on a determination result in the determining.

16. A blood coagulation analyzing apparatus comprising an analysis controller that perform operations comprising:
   calculating a coagulation time based on data representing a change in an optical detection value of a blood specimen added with a reagent for starting a coagulation reaction, the optical detection value representing amount of light transmitted through the blood specimen added with the reagent; and
   determining whether an early reaction error has occurred based on a comparison result obtained by comparing an index value related to derivatives calculated concerning a coagulation curve represented by the data, to a predetermined threshold, wherein the index value comprises at least one of:
   a time period from a first time point at which the reagent is added to a second time point at which a minimum value of a first derivative calculated concerning the coagulation curve is obtained;
   an absolute value of the minimum value of the first derivative calculated concerning the coagulation curve;
   an integral value of a difference between: the optical detection values in a time period from a third time point at which a predetermined time elapses from the first time point to a fourth time point at which a minimum value of a second derivative calculated concerning the coagulation curve is obtained; and the optical detection value at the third time point; or
   a ratio of:
   the difference between the optical detection value at the fourth time point and the optical detection value at the third time point; to
   a difference between an optical direction value at a fifth time point at which the coagulation reaction is regarded as stopped and the optical detection value at the third time point.

17. The blood coagulation analyzing apparatus according to claim 16, wherein the analysis controller performs operations further comprising outputting the coagulation time in an output form depending on a determination result in the determining.

18. A non-transitory computer-readable storage medium storing a computer program executable by a computer to perform operations comprising:
   calculating a coagulation time based on data representing a change in an optical detection value of a blood specimen added with a reagent for starting a coagulation reaction, the optical detection value representing amount of light transmitted through the blood specimen added with the reagent; and
   determining whether an early reaction error has occurred based on a comparison result obtained by comparing an index value related to derivatives calculated concerning a coagulation curve represented by the data, to a predetermined threshold, wherein the index value comprises at least one of:
   a time period from a first time point at which the reagent is added to a second time point at which a minimum value of a first derivative calculated concerning the coagulation curve is obtained;
   an absolute value of the minimum value of the first derivative calculated concerning the coagulation curve;
   an integral value of a difference between: the optical detection values in a time period from a third time point at which a predetermined time elapses from the first time point to a fourth time point at which a minimum value of a second derivative calculated concerning the coagulation curve is obtained; and the optical detection value at the third time point; or
   a ratio of:
   the difference between the optical detection value at the fourth time point and the optical detection value at the third time point; to
   a difference between an optical direction value at a fifth time point at which the coagulation reaction is regarded as stopped and the optical detection value at the third time point.

19. A blood coagulation analyzing method comprising:
   calculating a coagulation time based on data representing a change in an optical detection value of a blood specimen added with a reagent for starting a coagulation reaction, the optical detection value representing amount of light transmitted through the blood specimen added with the reagent; and
   outputting the coagulation time based on a comparison result obtained by comparing an index value related to derivatives calculated concerning a coagulation curve represented by the data used in the calculating the coagulation time, to a predetermined threshold, wherein the index value comprises at least one of:
   a time period from a first time point at which the reagent is added to a second time point at which a minimum value of a first derivative calculated concerning the coagulation curve is obtained;
   an absolute value of the minimum value of the first derivative calculated concerning the coagulation curve;
   an integral value of a difference between: the optical detection values in a time period from a third time point at which a predetermined time elapses from the first time point to a fourth time point at which a minimum value of a second derivative calculated concerning the coagulation curve is obtained; and the optical detection value at the third time point; or
   a ratio of:
   the difference between the optical detection value at the fourth time point and the optical detection value at the third time point; to
   a difference between an optical direction value at a fifth time point at which the coagulation reaction is regarded as stopped and the optical detection value at the third time point.

* * * * *